United States Patent [19]

Haberman et al.

[11] Patent Number: 4,988,446
[45] Date of Patent: * Jan. 29, 1991

[54] METHOD FOR SPECTROSCOPIC ANALYSIS OF HYDROCARBONS

[75] Inventors: Joel I. Haberman, Seabrook, Tex.; Robert E. Overfield, Calgary, Canada; Winston K. Robbins, New Providence, N.J.

[73] Assignee: Exxon Research and Engineering Company, Florham Park, N.J.

[*] Notice: The portion of the term of this patent subsequent to Sep. 12, 2006 has been disclaimed.

[21] Appl. No.: 358,779

[22] Filed: May 30, 1989

Related U.S. Application Data

[63] Continuation-in-part of Ser. No. 143,744, Jan. 14, 1988, Pat. No. 4,865,746, which is a continuation-in-part of Ser. No. 6,382, Jan. 23, 1987, abandoned.

[51] Int. Cl.$^5$ ............................................. B01D 15/08
[52] U.S. Cl. .................................. 210/656; 210/198.2; 73/61.1 C; 250/301; 250/373; 436/140; 436/143; 436/161
[58] Field of Search ............... 436/139, 140, 143, 161; 210/656, 659, 198.2; 73/61.1 C; 250/301, 373

[56] References Cited

U.S. PATENT DOCUMENTS

| | | | |
|---|---|---|---|
| 3,676,649 | 7/1972 | Burk | 73/61.1 C |
| 3,897,213 | 7/1975 | Stevens | 73/61.1 C |
| 3,975,727 | 8/1976 | Mader | 73/61.1 C |
| 4,199,323 | 4/1980 | Miller | 73/61.1 C |
| 4,254,656 | 3/1981 | Sanford | 73/61.1 C |
| 4,264,814 | 4/1981 | Freund | 250/373 |
| 4,265,634 | 5/1981 | Pohl | 73/61.1 C |
| 4,455,084 | 6/1984 | Webb | 73/61.1 C |
| 4,476,713 | 10/1984 | Alfredson | 73/61.1 C |
| 4,563,585 | 1/1986 | Ward | 250/373 |
| 4,567,753 | 2/1986 | Miller | 73/61.1 C |
| 4,614,871 | 9/1986 | Driscoll | 250/373 |
| 4,631,687 | 12/1986 | Kowalski | 73/61.1 C |
| 4,671,103 | 6/1987 | Dickakian | 73/61.1 C |
| 4,733,084 | 3/1988 | Oosaka | 250/373 |

OTHER PUBLICATIONS

Krstulovic, Selective Monitoring of Polynuclear Aromatic Hydrocarbons by High Pressure Liquid Chromatography with a Variable Wavelength Detector, Analytical Chemistry, vol. 48, No. 9, Aug. 1976, pp. 1383-1386.
Bollet et al., "Journal of Chromatography", vol. 206, pp. 289-300, 1981.
Hennion et al., "Journal of Chromatography", vol. 280, pp. 351-362, 1983.
Galya, Rapid Sara Separations by High Performance Liquid Chromatography, Journal of Liquid Chromatography, 3(2), pp. 229-242 (1980).
Klevens, Spectral Resemblances of Cata-Condensed Hydrocarbons, The Journal of Chemical Physics, vol. 17, No. 5, May 1949, pp. 470-481.
Miller, Automated Hydrocarbon-Type Separation by Multi-Dimensional Liquid Chromatography, Peteoanalysis 81, 1981, pp. 91-105.

Primary Examiner—Ernest G. Therkorn
Attorney, Agent, or Firm—Jay Simon

[57] ABSTRACT

A sample of a hydrocarbon oil containing asphaltenes is chromatographically analyzed by forming a mixture of the oil with a weak solvent. The mixture is passed in contact with a column of a stationary phase of fine solid particles of fully functionalized material, followed by a weak solvent. The solvent, after recovery from the column, is analyzed for aromatics by UV-absorption of UV radiation in the range 200 to 400 nm. The absorbance of the UV light by the irradiated eluents across the UV wavelength range is monitored and the integral of absorbance is derived as a function of photon energy across the wavelength range. The magnitude of the derived integral in at least one time interval corresponding with aromatics in the eluent from the stationary phase is measured as an indication of the level of aromatics in the oil sample. The weak solvent may be followed by a strong solvent which, in turn, may be followed by a strong solvent which is modified by the addition of a hydrogen bonding solvent.

23 Claims, 7 Drawing Sheets

NMR AROMATICITY COMPARISON DEMONSTRATES ACCURACY OF AROMATIC CORE DETECTOR

PREDICTED AROMATICITY = 1.0° AROMATIC CORES + 2.0° POLARS CORES

CHROMATOGRAM OF HEAVY ARABIAN VACUUM RESID

METHOD FOR SPECTROSCOPIC ANALYSIS OF HYDROCARBONS

CROSS REFERENCE TO RELATED APPLICATIONS

This application is a Continuation-In-Part of U. S. Serial No. 143,744, filed Jan. 14, 1988, now U.S. Pat. No. 4,865,746, which in turn is a Continuation-In-Part of U.S. Serial No. 006,382, filed Jan. 23, 1987, and now abandoned.

FIELD OF THE DISCLOSURE

This invention relates to a method for analyzing hydrocarbon containing oils and for using the results of the analysis to control various hydrocarbon refining processes. More particularly, this invention relates to a method for determining, with great particularity, the aromatic core content of hydrocarbon containing oils. Still more particularly, the aromatic core content of hydrocarbon containing oils is determined by integrating the UV light absorbance of the aromatic compounds into an energy function and comparing the absorbance integral with predetermined values and thereby obtain the aromatic core content.

In one embodiment of this invention the hydrocarbon oil may be separated into fractions by liquid chromatography, particularly known as high performance liquid chromatography (HPLC), wherein the separate fractions are monitored and absorbance integrals are determined as an energy function.

BACKGROUND OF THE INVENTION

Ultraviolet absorbance spectroscopy has been widely used to quantitatively detect levels of aromatic compounds in solution. Individual aromatic compounds have characteristic spectra which differ with ring size and substitution of the aromatic. The ultraviolet absorbance of the sample is proportional to the product of the molar concentration and the pathlength. The constant of proportionality is known as the extinction coefficient. The extinction coefficient varies widely among compounds. Therefore, two approaches to quantification of mixtures of aromatics have been taken. In one, the spectra of the individual compounds present are "deconvoluted" by mathematical analysis and simulation of the individual overlapping absorbance bonds. This method is limited to a small number (typically less than 10) of compounds in a mixture. If the nature of compounds is unknown, there is much uncertainty as to whether accurate levels are obtained. In the other approach, the extinction coefficients are replaced with "response factors" which characterize the average value of extinction coefficient which is expected to apply. When the relative proportions of compounds comprising the mixture changes, the "response factors" must also be changed.

Reference is made to Klevens and Platt, J. Chem. Phys. 17:470 (1949). Similarities are reported in the total oscillator strength for electronic transitions of cata-condensed aromatics. In that report, the similarities were used to support a theory for the quantum mechanical basis of electronic transitions in known structures. No realization was made that this method could be applied to measure the level of aromatic functionality in mixtures of unknown structures.

Furthermore, cata-condensed aromatics constitute only a minor fraction of the various aromatics in a hydrocarbon feedstock such as petroleum. Other aromatics, including peri-condensed aromatics, alkyl aromatics, naphtheno-aromatics and thiophenic aromatics which behave spectroscopically differently from cata-condensed aromatics, are also generally present in a hydrocarbon feedstock.

Also, the article does not relate to HPLC analysis, nor does it recognize or suggest that a UV detector operating in a specific wavelength range can be used in HPLC to derive an integrated oscillator strength output which quantifies the aromatic carbon in petroleum and shale oil feedstocks.

Chromatography is a well-documented and widely used laboratory technique for separating and identifying the components of a fluid mixture, e.g., a solution, and relies on the different relative affinities of the components between a stationary phase and a mobile phase which contacts the stationary phase.

In a typical example of chromatography, the stationary phase is a suitable particulate solid material which is substantially uniformly packed into a tube so as to form a column of the stationary phase material. The mobile phase may be the fluid under investigation, or more commonly, a solution of the fluid under investigation. The solvent used in the solution is usually first passed through the column of solid stationary phase and thereafter a small sample comprising a solution of the fluid under investigation is passed through the column, followed by solvent alone. The components of the fluid will have different affinities for the stationary phase and will therefore be retained at different regions along the length of the column for different times. For some components, the affinity will be so slight that virtually no retention is evident while for others, the affinity might be so great that the components are not recovered from the column even after considerable periods of time have elapsed since they were introduced into the column and subjected to the potential eluding properties of the solvent.

Petroanalysis 81, Chapter 9, discloses that a hydrocarbon mixture combined with a solvent results in an eluate being recovered from the exit end of a chromatographic column which comprises the following types of molecular species, in order, namely: saturates (e.g., paraffins and naphthenes), olefins and aromatics. The remaining molecular species, generally polar compounds, have a relatively high affinity for the solid chromatographic material and can only be recovered in a reasonable time and reasonably completely by interrupting the flow of the solvent and substituting a different solvent having a relatively high affinity for, e.g., heteroaromatic compounds. The different solvent is passed through the column in a direction opposite to that of the first solvent (back-flushing) so that after a reasonable time interval, polar compounds (resins) are present in the back-flush eluate. The change in solvent from the first solvent, pentane, to the second solvent, methyl t-butylether, necessitates the use of two different eluent detectors, i.e., one using refractive index and the other using ultra-violet absorbance at 300 nm.

In Journal of Liquid Chromatography, 3(2), 229-242 (1980), a hydrocarbon mixture containing asphaltenes is subjected to chromatographic analysis only after mixing with hexane to precipitate asphaltenes which are separated by filtration and then determined gravimetrically. The hexane solution of the remaining hydrocarbons is then passed through a column of particles of u-Bondapak-NH$_2$ where it separates into an eluent comprising, initially, saturates and then aromatics, as determined by the refractive index of the eluent. Resin which is retained on the column is backflushed off the column and determined by difference. The separation quality of the column is maintained by flushing it with a solution of 1/1 methylene chloride/acetone after every 20 samples and then regenerating with methylene chloride and hexane for repeatable retention times. Changes in the refractive index of the eluents, indicative of the presence of respective chemical species, are monitored and correlated with absolute amounts of the chemical species by means of a Hewlett-Packard 3354B computer using the so-called "Zero" type method.

In Journal of Chromatography, 206 (1981) 289–300, Bollet et al., a rapid high-performance liquid chromatography technique for separating heavy petroleum products into saturated, aromatic and polar compounds is described. A column containing a stationary phase of silica bonded NH$_2$ ("Lichrosorb NH$_2$") is used. Two chromatographic analyses are needed in order to determine the composition of a sample. In the first analysis, saturated compounds are separated from aromatic and polar compounds, using hexane or cyclohexane as the mobile phase. In the second analysis, saturated and aromatic compounds are separated from polar compounds using 85 vol% cyclohexane, 15 vol% chloroform as the mobile phase. The eluents are monitored by differential refractometry for saturated, aromatic and polar compounds, and by ultraviolet photometry for polar compounds. The proportions of saturated and polar compounds are said to be determinable by these monitoring techniques and the proportion of aromatic compounds found by difference. However, the method described, in common with all other reports of high performance liquid chromatography for analysis of samples of heavy hydrocarbon oil mixtures, is limited by the lack of a means and method for quantitative and feedstock-independent detection and monitoring. Thus, for both refractive index (RI) and ultraviolet (UV) detectors, "response factors" must be derived by separating samples of the feedstock on a larger scale, known in the art as "semi-preparative liquid chromatography" and then gravimetrically weighing the recovered analyte (after removal of the solvent(s) added to the sample for the purpose of the chromatographic separation). Response factors are dependent on the nature of the feedstock and its boiling range, and it is therefore essential to perform the relatively large-scale separation to obtain accurate results with the HPLC analysis. Thus, the potential benefits of speed and increased resolution which should be possible with HPLC have not heretofore been fully realized in practice.

SUMMARY OF THE INVENTION

It is an object of the present invention to provide a simpler, more comprehensive and more accurate method for analyzing mixtures of aromatic compounds (particularly, but not exclusively, mixtures of hydrocarbons) by ultraviolet spectroscopy.

It is another objective of the present invention to quantify the aromatic core content of a solution of a mixture of aromatics but also, by using liquid chromatography with ultraviolet spectroscopic detection, to determine the aromatic core content of individual fractions of the mixture including the saturates, aromatics, and polars in the hydrocarbon oil and, further, to use this information, along with the quantitative levels of all components, to determine the extent of saturated substitution of aromatic and polar components.

It is also an object of the invention to provide a process for refining and/or upgrading hydrocarbons using novel spectroscopic and/or chromatographic methods to regulate or optimize said process.

Aromatic functionality may exist in several types of molecules in hydrocarbon containing samples such as, for example, petroleum, intermediate streams in petroleum refining, finished petroleum products, as well as certain feeds, intermediates, and finished products in the production of Chemicals and pharmaceuticals.

These molecules with aromatic functionality include alkyl-substituted aromatics and naphthene-substituted aromatics. Only the aromatic portion of these molecules, with delocalized pi electrons, absorbs radiation in the ultraviolet region of the spectrum. The aromatic portion of the molecule is referred to as the "aromatic core". For example, in tetrahydronaphthalene, the aromatic core is benzene and the other four carbons form a naphthenic ring. In xylene, the aromatic core is again benzene while the two methyl groups are alkyl substitutes. With heteroaromatic molecules, the heteroatom is part of the core if it contributes pi electrons to the aromatic system. Therefore, in dibenzothiophene the sulfur counts as a member of the aromatic core, even though it is not a carbon. While counting the sulfur as a member of the aromatic core introduces a slight error into the results, this error is insubstantial and may be ignored because the amount of sulfur in heteroaromatics is quite low. Also, the error can be corrected by knowing the amount of thiophenic sulfur in the sample.

According to the present invention there is provided a method for the spectroscopic analysis of solutions containing at least two aromatic compounds for the aromatic core content comprising the steps of:
(a) irradiating the solution with UV light having a wavelength range of which at least a portion is within the range of about 200 nm to about 500 nm,
(b) measuring the absorbance of the UV light by the aromatic cores in the solution,
(c) deriving the integral of absorbance as a function of photon energy across the energy corresponding to the wavelength range; and
(d) comparing the absorbance integral to a predetermined value, thereby obtaining the aromatic core content.

The spectrographic analysis is applicable to any petroleum, coal or shale oil fraction including, but not limited to, whole crude, topped crude, any atmospheric or vacuum distillate, and any converted or unconverted feed stream which contains at least two aromatics.

DESCRIPTION OF THE DRAWINGS

The invention is now further described by way of example with reference to the drawings in which.

DETAILED DESCRIPTION OF THE INVENTION

Figure 1:
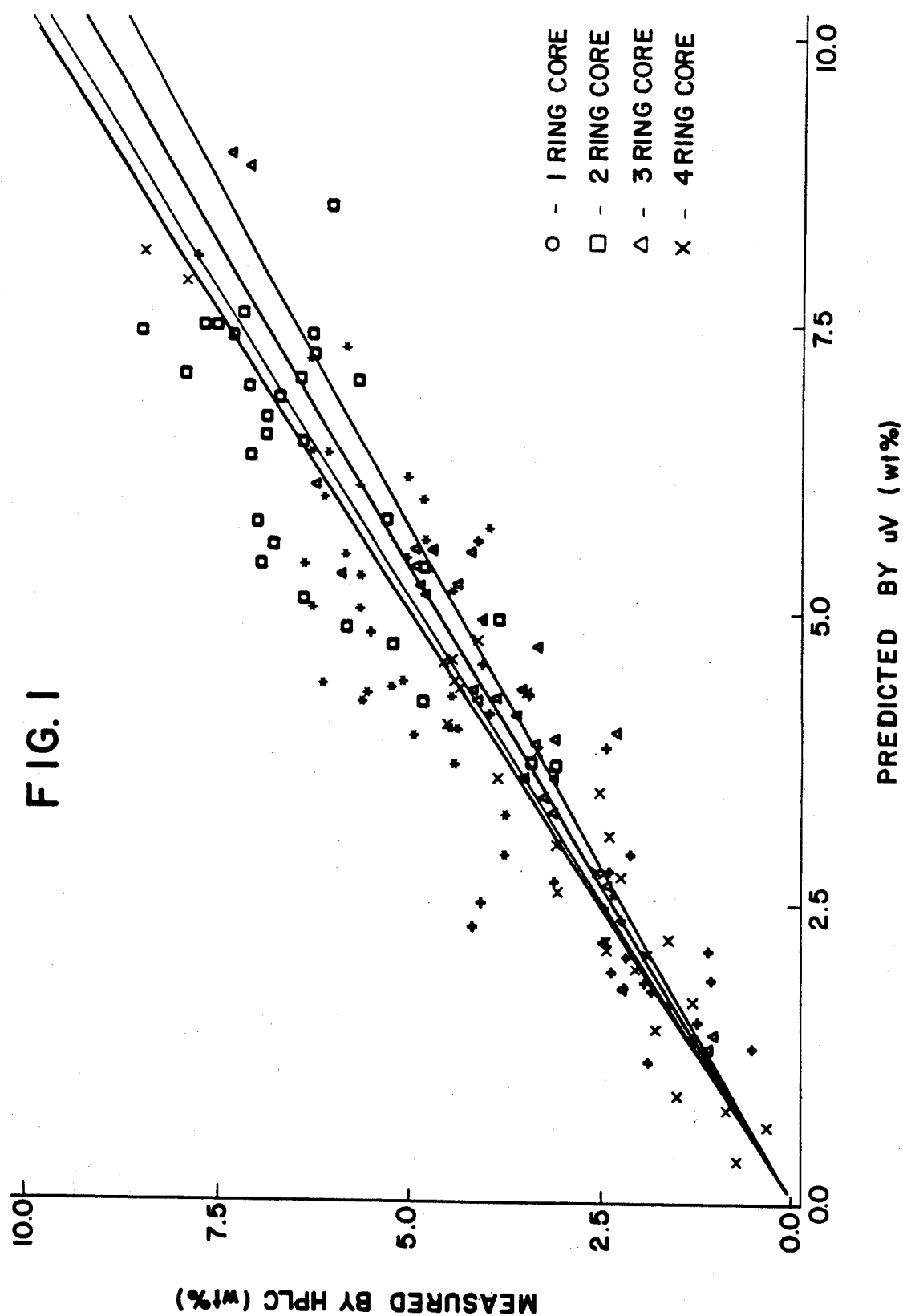
FIG. 1 is a regression-analysis graph of the weight percent of aromatic core in 1, 2, 3, or 4 ring structures as determined by HPLC method A (on the abscissa) versus the predicted weight percent aromatic core in 1, 2, 3 or 4 ring structures as derived from a linear combination of oscillator strengths in discrete portions as described herein.

In the particular description herein, only those features which have a direct bearing on the disclosed embodiments of the invention will be mentioned; features which will be well-known to those skilled in the art will not be referred to.

It is common knowledge that many compounds, aromatic compounds in particular, absorb ultraviolet light and that the degree of absorption (A) of ultraviolet light may be quantitatively related to the molar concentration of said compound and the pathlength ($\lambda$) of sample through which the light passes by Beer's Law:

$$A = a \cdot C \cdot \lambda$$

The constant of proportionality ($a$) is known as the extinction coefficient; C is the molar concentration of the compound.

This measurement may be performed with either a commercially available UV spectrophotometer or with a custom made instrument. The essential elements of the device are a lamp or other source of UV radiation, optics to direct that light through the sample, and a detector such as a photomultiplier or photo sensitive diode which responds with a signal which is proportional to the intensity of light detected. The absorbance by the sample is given by the negative logarithm of the ratio of the intensity measured with (I) and without ($I_o$) the sample in place:

$$A = -\log_{10} \frac{(I)}{(I_o)}$$

The absorbance at a given wavelength is determined by refracting or diffracting the light to allow only the wavelength range of interest to pass through the sample at one time, or by allowing the full spectra to pass through and then refracting or diffracting the light so that only the desired wavelength range is measured by a detector at a given time.

A limitation to this method is that differences in molecular structure, such as number of rings or type of substitution, change the ultraviolet absorbance spectrum of the compound and change the extinction coefficient. As an example of this limitation, consider the well known, highly variant extinction coefficients for some aromatic molecules for ultraviolet light of 254 nm wavelength:

| Compound | $a$ ($M^{-1}$ $cm^{-1}$) at 254 nm |
|---|---|
| Benzene | 20 |
| Toluene | 200 |
| Biphenyl | 14,000 |
| Naphthalene | 3,000 |
| Anthracene | 150,000 |
| Phenanthrene | 50,000 |
| Pyrene | 16,500 |
| Dibenzanthracene | 3,000 |

In a solution that contains a mixture of aromatic compounds, it is not possible to choose an extinction coefficient which relates the ultraviolet absorbance to the total molar concentration of aromatics.

It has been found that while the extinction coefficient at a single wavelength is highly variant for differing aromatic compounds, the integral of absorbance over the photon energy in the ultraviolet region of the spectrum produces a quantity which is largely invariant with the molar concentration of aromatic carbon for the types of aromatics and heteroaromatics which are found in hydrocarbon oils. The photon energy ($\epsilon$) is related to the wavelength by:

$$\epsilon = \frac{hc}{\lambda}$$

Where h is Plank's constant, c is the speed of light, and $\lambda$ is the wavelength. A preferred way to practice the invention is to measure the integral of absorbance over photon energy in place of the absorbance at a single wavelength or small number of wavelengths.

This produces a quantity referred to as the integrated oscillator strength (Q). The quantity Q is defined as:

$$Q = \int A(\epsilon) \, d\epsilon \qquad (1)$$

where:
A = absorbance
$\epsilon$ = photon energy
and the integral is taken over an energy range corresponding to a wavelength range from 200 to 500 nm A preferred way in which Q can be determined will now be described, in the case of a diode array detector. Each detector produces an output signal proportional to the intensity, I, of the light it detects. A computer converts each detector output to a quantity A($\lambda$)—i.e., absorbance, where $\lambda$ represents wavelength—where A = $-\log_{10}(I/I_o)$, $I_o$ being the intensity of the UV source without the sample in place. The bandwidth $\Delta\lambda$, received by each individual detector in the detector array, is the same (e.g., 2 nm) but the wavelength varies (by an increment or decrement equal to the bandwidth) from each detector to the next. Therefore, the computer multiplies the quantity A($\lambda$) by a weighting factor $$E(\lambda) = hc \left[ \frac{1}{\lambda - 0.5\,(\Delta\lambda)} - \frac{1}{\lambda + 0.5\,(\Delta\lambda)} \right],$$

and sums across the UV spectrum to derive the integrated oscillator strength Q.

The validity and accuracy of this approach has been established by comparison to model components.

The ultraviolet spectra of a series of known compounds was measured from 200 to 500 nm. These were dissolved at known concentrations in cyclohexane, a solvent which is substantially transparent to light in this wavelength range. This solution is placed in a 1 mm pathlength cell and irradiated with light having a wavelength of 200 to 500 nm with a conventional UV/visible spectrophotometer. The absorbance is measured as a function of wavelength.

The absorbance as a function of wavelength was transformed to the absorbance as a function of energy by the relationship of $\epsilon$ to $\lambda$, and the resultant function was integrated over the full range of wavelength from 200 to 500 nm as described above. The results are shown in Table I.

TABLE I
INTEGRATED OSCILLATOR STRENGTHS FOR MODEL COMPOUNDS

|  | eV/mV·cm (Compound Basis) | eV/mM-cm (Per Aromatic Carbon) |
|---|---|---|
| A. Simple Substitution for Naphthalenes |  | (10 $C_a$) |
| 1. Naphthalene | 32.9 | 3.29 |
| 2. Methylnaphthalene | 34.0 | 3.40 |
| 3. Methylnaphthalene | 35.2 | 3.52 |
| 4. 2-Ethylnaphthalene | 40.8 | 4.08 |
| 5. 1,4-Dimethylnaphthalene | 37.0 | 3.70 |
| 6. n-Butylnaphthalene | 39.0 | 3.90 |
| 7. Hexahydropyrene (Aldrich) | 35.4 | 3.54 |
| 8. Hexahydropyrene (Rutgers) | 34.0 | 3.40 |
| 9. Diamylnaphthalene | 39.7 | 3.97 |
| 10. 1α-Pentadecylnaphthalene | 37.6 | 3.76 |
| 11. Hexadecylnaphthalene | 36.4 | 3.64 |
| 12. "$C_{16}$ Naphthalene" | 47.8 | 4.78 |
| 13. 1-α-Octadecylnaphthalene | 41.8 | 4.18 |
| Mean (±1σ) | 37.8 (±4.06) | 3.78 (±0.4) |
| B. 3-Ring Aromatics |  | (14$C_a$) |
| 1. Phenanthrene | 42.2 | 3.01 |
| 2. 1-Methylphenanthrene | 46.0 | 3.28 |
| 3. 2-Methylphenanthrene | 51.2 | 3.66 |
| 4. 3-Methylphenanthrene | 46.2 | 3.30 |
| 5. Retene | 58.1 | 4.15 |
| 6. 2,3 Dihydro-1H-cyclopenta (l) phenanthrene | 45.6 | 3.26 |
| 7. Octadecylphenanthrene | 46.5 | 3.32 |
| 8. Dibenzothiophene | 39.6 | 2.83 |
| Mean (±σ) | 46.9 (±5.64) | 3.35 (±0.40) |
| C. 4-Ring Peri Condensed Aromatics |  | (18$C_a$) |
| 1. Fluoranthene | 57.1 | 3.57 |
| 2. Pyrene | 55.0 | 3.44 |
| 3. 1 Methylpyrene | 51.6 | 3.22 |
| 4. 1,9 Dimethylpyrene | 64.9 | 4.06 |
| 5. n-Butylpyrene | 56.9 | 3.55 |
| Mean (±σ) | 57.1 (±4.89) | 3.57 (±0.35) |
| D. 4-Ring Cata Condensed Aromatics |  | (22$C_a$) |
| 1. Triphenylene | 57.6 | 3.20 |
| 2. Chrysene | 44.3 | 2.46 |
| 3. Benz(a)anthracene | 73.3 | 4.07 |
| 4. Benzodiphenylene sulfide | 57.4 | 3.19 |
| 5. 5,6 Dihydro-4H-dibenz (a,kl) anthracene | 56.8 | 3.15 |
| Mean (±σ) | 57.9 (±10.3) | 3.22 (±0.57) |

It can be seen that the integrated oscillator strength, Q, per aromatic carbon, is very nearly constant. This allows the total aromatic core content to be measured even in solutions which contain mixtures of aromatics with varying structure, ring size, and substitution.

The various types of aromatics for which this measurement is applicable include cata-condensed aromatics, peri-condensed aromatics, alkyl-substituted aromatics, naphtheno-aromatics, and heteroaromatics such as thiophenic aromatics, carbazols, and the like.

Another object of the invention is to provide a method, using ultraviolet spectroscopy, to determine the types of aromatic structures in solutions containing aromatics. This is important for process control, since differing aromatic structures generally behave differently in the separation or reaction process which is being controlled. For example, the detection of aromatic cores is important in many refinery processes. In the production of jet fuels, aromatics control the smoke point. In mogas they give high octane and in diesel low cetane. In cat-cracking, multi-ring aromatics (PNA's) and heteroaromatics (Polars) are important because they limit crackability and add to coke make. In lubes production, multi-ring (2 and higher) aromatics give low viscosity index (VI).

The aromatic ring size distribution is a useful measure of the aromatic core structure. The aromatic ring size distribution is the weight percent of aromatic core that occurs as 1 ring, 2 condensed rings, 3 condensed rings, and 4 condensed rings. This information is typically derived from mass spectroscopy or from high performance liquid chromatography. An advantage is obtained in determining this information from ultraviolet spectroscopy.

Since ultraviolet spectroscopy is a rapid procedure and relatively easy to automate, it may be used as an "on-line" analytical measurement.

It was found that the aromatic ring distribution could be determined from the oscillator strength, Q, measured over a number of discrete energy ranges. Following the principals leading to equation (1) above, a new variable, $Q(\lambda)$, is defined as follows:

$$Q(\lambda) = A(\lambda) \cdot \left[ \frac{1240}{(\lambda - 1)} - \frac{1240}{(\lambda + 1)} \right]$$

Where: $A(\lambda)$ = optical absorbance at wavelength $\lambda$.

Thus, $Q(\lambda)$ represents a discrete portion of the function Q where the absorbance is integrated over an energy region corresponding to the wavelength region of $(\lambda - 1)$ to $(\lambda + 1)$ nm.

To derive the relationships between $Q(\lambda)$ and the aromatic ring size distribution, 32 samples of heavy petroleum oils were dissolved in hexane and their ultraviolet spectra were measured from 200 to 400 nm. The spectra were converted to discrete oscillator strength elements ($Q(\lambda)$ at $\lambda = 202, 204, 206, \ldots 398$) and combined with the compositional data for each sample obtained via HPLC Method A described below to form a statistical data base. The heavy oils tested include virgin distillates, hydrotreated distillates, thermally treated distillates, and a vacuum resid. Using linear regression techniques the following equations were developed to predict the various components as they are measured by HPLC.

1 Ring
Aromatics = $-174.6*Q(204) + 229.0*Q(206) - 151.5*Q(288)$

2 Ring
Aromatics = $23.3*Q(216) + 32.8*Q(236) - 38.5*Q(334)$

3 Ring
Aromatics = $173.1*Q(252) - 110.1*Q(262) - 185.58*Q(334)$

4 Ring
Aromatics = $-18.1*Q(234) + 64.3*Q(260) + 9966*Q(386) - 10629*Q(392)$

Table II gives the results of this technique on 31 typical feeds. The Standard Errors are on the order of 1% which is within the error of the HPLC data. Also shown on this table are the HPLC data (AR1...AR4), predicted data (PAR1...PAR4), and the difference (EAR1...EAR4) between the predicted data from UV only and the HPLC data.

(a) passing a mixture of the hydrocarbon oil and a carrier phase in contact with a chromatographic stationary phase over a first time interval so as to retain components of said hydrocarbon oil on said stationary phase;

(b) passing a mobile phase in contact with said stationary phase after step (a) over a second time interval, for eluting different retained components of said oil from said stationary phase at different time intervals, and recovering the mobile phase which has contacted the stationary phase together with the components eluted from the stationary phase;

(c) irradiating the recovered mobile phase with UV light having a wavelength range of which at least a part is within about 200 nm to about 500 nm over a sufficient time period that the recovered components in the recovered mobile phase are subjected to said irradiation, said mobile phase being substantially transparent to UV light within said wavelength range;

(d) monitoring the absorbance of said UV light by said irradiated components across said wavelength range and deriving the integral of absorbance as a function of photon energy across said wavelength range; and (e) measuring the magnitude of said derived integral in at least one selected time interval corresponding with

TABLE II

| VARIABLE | N | SAS MEAN | STD ERROR |
|---|---|---|---|
| EAR1 | 31 | 0.12292289 | 0.89852904 |
| EAR2 | 31 | 0.07188635 | 1.13750991 |
| EAR3 | 31 | −0.56747095 | 0.65789982 |
| EAR4 | 31 | −0.01237452 | 0.52235894 |

| SAMP_NUM | AR1 | PAR1 | EAR1 | AR2 | PAR2 | EAR2 | AR3 | PAR3 | EAR3 | AR4 | PAR4 | EAR4 |
|---|---|---|---|---|---|---|---|---|---|---|---|---|
| FS-4815 | 4.35 | 3.62 | 0.73 | 5.24 | 5.71 | −0.47 | 3.06 | 3.22 | −0.16 | 2.35 | 2.05 | 0.30 |
| FS-4914 | 4.97 | 6.09 | −1.11 | 6.23 | 7.30 | −1.07 | 4.14 | 5.45 | −1.31 | 2.38 | 2.71 | −0.34 |
| FS-4999 | . | 3.06 | . | . | 7.71 | . | . | 14.55 | . | . | 27.69 | . |
| FS-5020 | 4.97 | 5.39 | −0.43 | 6.36 | 6.38 | −0.02 | 3.99 | 4.87 | −0.88 | 3.01 | 2.95 | 0.06 |
| FS-5074 | 2.25 | 2.53 | −0.28 | 5.99 | 8.41 | −2.42 | 10.40 | 12.74 | −2.34 | 24.13 | 23.78 | 0.35 |
| FS-5075 | 4.31 | 3.92 | 0.39 | 5.64 | 6.91 | −1.28 | 3.48 | 4.27 | −0.80 | 3.79 | 3.51 | 0.28 |
| FS-5078 | 4.38 | 5.11 | −0.73 | 6.39 | 6.92 | −0.52 | 3.55 | 4.05 | −0.50 | 1.44 | 0.80 | 0.63 |
| FS-5108 | 5.01 | 4.32 | 0.69 | 6.21 | 7.13 | −0.92 | 3.27 | 4.64 | −1.37 | 2.99 | 2.55 | 0.45 |
| FS-5168 | 5.55 | 4.14 | 1.40 | 11.30 | 8.53 | 2.78 | 7.35 | 8.85 | −1.50 | 8.47 | 8.00 | 0.47 |
| FS-5335 | 3.90 | 5.65 | −1.75 | 7.51 | 10.16 | −2.64 | 7.10 | 8.74 | −1.64 | 7.91 | 7.75 | 0.16 |
| FS-5525 | 3.69 | 2.87 | 0.82 | 5.15 | 4.63 | 0.51 | 3.04 | 3.84 | −0.80 | 3.41 | 4.24 | −0.83 |
| FS-5550 | 5.78 | 5.42 | 0.36 | 3.02 | 3.62 | −0.59 | 0.96 | 1.33 | −0.37 | 0.66 | 0.26 | 0.40 |
| FS-5579 | 4.64 | 5.47 | −0.83 | 7.51 | 7.36 | 0.15 | 5.83 | 5.25 | 0.58 | 4.05 | 4.68 | −0.64 |
| FS-5581 | 6.26 | 7.09 | −0.83 | 7.68 | 7.37 | 0.31 | 4.11 | 4.26 | −0.15 | 2.48 | 2.72 | −0.25 |
| FS-5585 | 5.59 | 4.94 | 0.65 | 3.35 | 3.64 | −0.29 | 1.03 | 1.22 | −0.19 | 0.26 | 0.55 | −0.29 |
| FS-5586 | 5.48 | 4.22 | 1.26 | 4.74 | 5.31 | −0.56 | 2.35 | 2.61 | −0.26 | 1.22 | 1.62 | −0.40 |
| FS-5588 | 5.17 | 4.27 | 0.90 | 6.72 | 5.49 | 1.23 | 4.32 | 5.17 | −0.85 | 3.26 | 3.74 | −0.48 |
| FS-5608 | 3.68 | 3.21 | 0.47 | 3.77 | 4.86 | −1.10 | 2.22 | 3.91 | −1.69 | 2.44 | 3.39 | −0.95 |
| NCPD0101 | 6.21 | 4.95 | 1.25 | 5.76 | 4.79 | 0.97 | 2.16 | 1.72 | 0.44 | 1.25 | −0.35 | 1.60 |
| NCPD0109 | 6.07 | 4.31 | 1.76 | 7.04 | 6.25 | 0.79 | 3.06 | 3.51 | −0.45 | 1.53 | 2.16 | −0.63 |
| W-7503 | 6.05 | 5.90 | 0.15 | 7.29 | 7.28 | 0.01 | 4.05 | 4.17 | −0.12 | 2.16 | 2.68 | −0.52 |
| W-7504 | 5.79 | 7.20 | −1.41 | 8.49 | 7.30 | 1.19 | 6.19 | 6.01 | 0.17 | 4.28 | 4.27 | 0.00 |
| W-7507 | 6.23 | 6.30 | −0.07 | 7.91 | 6.94 | 0.98 | 4.73 | 5.07 | −0.34 | 2.36 | 2.12 | 0.24 |
| W-7508 | 5.58 | 5.23 | 0.35 | 4.75 | 4.15 | 0.61 | 2.41 | 2.11 | 0.30 | 0.79 | 0.69 | 0.11 |
| 1114 | 4.77 | 5.89 | −1.13 | 6.66 | 6.76 | −0.10 | 4.64 | 5.46 | −0.82 | 4.44 | 3.96 | 0.49 |
| 1124 | 6.32 | 5.33 | 0.99 | 6.33 | 5.03 | 1.30 | 3.18 | 3.35 | −0.17 | 1.72 | 1.37 | 0.34 |
| 1214 | 4.87 | 3.86 | 1.01 | 6.84 | 6.43 | 0.41 | 4.80 | 5.15 | −0.35 | 4.49 | 4.49 | 0.01 |
| 1224 | 6.02 | 6.29 | −0.27 | 6.83 | 6.59 | 0.24 | 3.30 | 3.80 | −0.50 | 1.82 | 2.02 | −0.20 |
| 1314 | 4.38 | 4.20 | 0.19 | 6.94 | 5.68 | 1.27 | 4.86 | 5.32 | −0.46 | 4.38 | 4.52 | −0.14 |
| 1324 | 5.61 | 6.01 | −0.40 | 7.07 | 6.85 | 0.23 | 3.44 | 3.52 | −0.08 | 1.98 | 1.89 | 0.09 |
| 1414 | 4.40 | 3.92 | 0.48 | 6.88 | 5.32 | 1.56 | 4.87 | 5.47 | −0.60 | 4.35 | 4.33 | 0.02 |
| 1424 | 4.72 | 5.54 | −0.81 | 7.16 | 7.48 | −0.32 | 3.81 | 4.19 | −0.38 | 2.30 | 3.03 | −0.73 |

FIG. 1 of the drawings shows the plots of the predicted vs. actual values for the samples in the data set.

According to the present invention from one aspect there is provided a method for analyzing hydrocarbon oil, which includes chromatography and comprises the steps of:

the elution of one or more components.

The mobile phase and the carrier phase can be liquids or gases or supercritical fluids. Usually they will be liquids.

In a preferred way of performing the invention the recovered mobile phase from the stationary phase is irradiated with UV light having a wavelength range within the range 230 to 500 nm. A scaling factor of 2 is applied to the derivation of the integral of absorbance so that the magnitude of said derived integral of absorbance is doubled, and said magnitude is measured in step (e) in a time interval corresponding with polar components in said mobile phase recovered from the stationary phase.

In a preferred way of putting the invention into effect, the absorbance of said UV light by said irradiated components is monitored using a diode array detector.

The present invention is also concerned with calibration so as to determine the different ring-numbers of aromatics present in the hydrocarbon oil. Calibration is achieved essentially by testing a sample of hydrocarbon oil according to the method as disclosed herein having known aromatic rings present, so as to associate the different times at which the different aromatics elute from the stationary phase with the ring-numbers of those different aromatics. This technique is described in more detail below.

One preferred way of performing the present invention provides a method of chromatographic analysis (Method A) of a hydrocarbon oil, which may or may not contain asphaltenes, comprising the steps of:

(a) forming a mixture of a sample of the oil with a weak solvent having a solubility parameter in the range of from 7.6 to 8.8 $cal^{0.5}/cm^{1.5}$;

(b) passing the said mixture in contact with a solid chromatographic stationary phase selected from:
   (i) a solid chromatographic stationary phase having surface hydroxyl groups of which substantially all have been substantially fully functionalized by at least one funtionalizing group selected from at least the following functionalizing groups: $-NH_2$, $-CN$, $-NO_2$, a charge-transfer adsorbent, a charge-transfer adsorbent functionalized with trinitroanilino-propane or tetranitrofluorenone, a homologue of any one of the foregoing, and a combination of two or more of the foregoing;
   (ii) a solid chromatographic stationary phase having a coronene capacity factor, with a mobile phase comprising cyclohexane and 0.03 vol% isopropanol, not exceeding 5.0 (preferably 2.5 or less); and
   (iii) a solid chromatographic phase comprising a combination of features of (i) and (ii);

(c) passing in contact with the said solid chromatographic stationary phase a weak solvent (preferably cyclohexane) having a solubility parameter in the range of from 7.6 to 8.8 $cal^{0.5}/cm^{1.5}$ for a first time period at least during and after step (b) and recovering the weak solvent which has contacted the solid stationary phase;

(d) monitoring the weak solvent recovered in step (c) for a second time period comprising at least a time interval after the first time period to detect eluent comprising any aromatic hydrocarbons;

(e) monitoring the weak solvent recovered in step (c) to detect eluent comprising any saturated hydrocarbons simultaneously with step (d) and after step (d);

(f) passing in contact with the said solid chromatographic stationary phase a strong solvent having a solubility parameter in the range of from 8.9 to 10.0 for a third time period which is at least after the second time period and recovering strong solvent which has contacted the said stationary phase;

(g) monitoring the strong solvent recovered in step (f) to detect eluent comprising any heteroaromatic compounds, polar compounds and asphaltenic materials;

(h) passing in contact with the said solid chromatographic stationary phase for a fourth time period which is at least after the third time period a strong solvent modified with a hydrogen-bonding solvent (such as an alcohol) which is miscible with the strong solvent, and recovering strong modified solvent which has contacted the said stationary phase; and (i) monitoring the recovered strong modified solvent recovered in step (h) to detect any eluent comprising moieties selected from at least one of the group consisting of polar compounds and asphaltenic materials.

Preferably, the change from weak solvent to strong solvent is effected over a finite period of time, i.e., there is a progressive change in solvent rather than a step change. It is found that superior separation is achieved in this way.

Preferably, step (j) is effected after step (i) by passing a weak solvent in said one direction in contact with the said stationary phase for a fifth time period which is at least after the fourth time period, said weak solvent preferably being the same as, or fully miscible with, the weak solvent of step (c). Preferably after step (j), steps (a) to (j) are repeated as described herein using another oil sample in step (a).

Another preferred way of performing the present invention also provides a method of chromatographic analysis (Method B) of a hydrocarbon oil, which may or may not contain asphaltenes, comprising the steps of:

(a) Forming a solution of a sample of the oil with a weak solvent having a solubility parameter in the range from 7.6 to 8.9 $cal^{0.5}/cm^{1.5}$.

(b) Passing the solution serially through two chromatographic columns (each mounted with appropriate switching mechanisms) in a sequence with:
   (i) the first chromatographic stationary phase having surface hydroxyl groups of which substantially all have been fully functionalized with a charge transfer functionality such as trinitroanilinopropane, tetrachlorophthalimidopropane, dinitrobenzoylglycidylpropane, tetranitrofluorenone, preferably dinitroanilinopropane.
   (ii) the second chromatographic stationary phase having surface hydroxyl groups of which at least a portion have been functionalized by at least one of the following functionalizing groups: aminopropyl, cyanopropyl, nitropropyl or a combination of the same, preferably a mixed cyano-amino functionality.

(c) Passing in contact with said serial solid stationary phases a weak solvent (preferably n-hexane) having a solubility parameter in the range from 7.0 to 7.8 $cal^{0.5}/cm^{1.5}$ for a time period at least during and after step (b) with the weak solvent being maintained dry.

(d) Passing the weak solvent through both solid stationary phases for a time interval sufficient to allow the saturates and mono-aromatics to elute from the first column;

(e) Bypassing the first column and continuing the weak solvent flow through the second column for a third time interval sufficient to complete the elution of the mono-aromatics after their separation from the saturates; the saturates elute first from the second column followed by the mono-aromatics.

(f) Returning the weak solvent flow to the first column and bypassing the second column.

(g) Continuing passing the weak solvent flow through the first column for a fourth time interval sufficient to elute the 2-ring aromatic compounds from the first column.

(h) Continuing to pass the weak solvent through the first column while increasing solvent strength at constant flow rate by replacing a portion of the weak solvent with a dry strong solvent with a solubility parameter in the range 8.9 to 10.0 cal$^{0.5}$/cm$^{1.5}$ in a step gradient function sufficient to initiate the rapid elution of three ring aromatics as a sharp peak for improved detection and continuing this elution for a fifth time interval sufficient to elute substantially all of the three ring aromatic components.

Traditionally, the solvent strength is changed by adding the strong solvent to the weak solvent in a linear gradient. In a preferred embodiment, the solvent strength is increased in a step function, so that the solvent composition is essentially instantaneously changed by the introduction of a greater amount of strong solvent at constant solvent flow rate, i.e., by replacing weak solvent with strong solvent. In a particularly preferred embodiment, the three ring aromatics are "chromatofocused" into a sharp peak using a saw tooth type gradient that sufficiently increases solvent strength to remove the three ring aromatics then drops to 20–50% (e.g., 40%) of its maximum to minimize the leading edge of the four ring aromatic components.

(i) Repeating step (h) except that a larger portion of the weak solvent is replaced by the strong solvent to initiate the rapid elution of four ring aromatics as a sharp peak for improved detection and continuing the elution for a sixth time interval sufficient to elute substantially all of the four ring aromatic components. The four ring aromatics are "chromatofocused" into a sharp peak with the saw tooth type gradient that increases solvent strength (preferably at constant flow rate, as described above) then drops to 70–90% (e.g., 80%) of its maximum to minimize the leading edge of the polar compounds.

(j) Continuing to pass the solvent mixture through the first column while sharply increasing the solvent strength by further increasing the portion of strong solvent (preferably at constant flow rate, as described above) and including a hydrogen bonding solvent (such as an alcohol; e.g., isopropyl alcohol) which is miscible with the strong solvent for a seventh time period sufficient to complete the elution of all the polar material from the first column:

(k) Passing the strong solvent over the first column for an eighth time interval sufficient to remove the hydrogen bonding solvent to a level of dynamic equilibrium;

(l) Passing the weak solvent over the first column for a ninth time interval sufficient to remove substantially all of the strong solvent, preferably at least 98% or 99% of the strong solvent is removed;

(m) switching the valve on the second column to allow the weak solvent to flow serially through both columns for a tenth time interval sufficient to allow both columns to return substantially to their initial activity.

(n) Monitoring the column eluents for the aromatic carbon content over the second through the seventh time periods with a detector positioned at the outlet of the serial columns;

(o) monitoring the mass of the column eluents over the second through the seventh time interval simultaneously with step (n) with a second detector (after the eluent has passed through the first detector).

If there are no 3-ring or 4-ring aromatics or polars in the hydrocarbon oil, these compounds will not elute and increasing solvent strength or adding a hydrogen binding solvent will not be necessary. Thus, the method can be generically described as increasing solvent strength n+2 times in n+2 intervals to elute compounds having n+2 aromatic rings, where n may be 0, 1, or 2, from the first stationary phase.

It has been found that this combination of valve switching and solvent chromatofocusing provides a superior ring distribution.

Preferably after step (j), steps (k)–(m) regenerate the column to its initial dynamic equilibrium and steps (a) through (j) are repeated as described herein using another oil sample in step (a).

In this second embodiment (Method B), the weak and strong solvents are maintained in a dry state by storage of the solvents over sufficient 4A molecular sieves to maintain water concentrations of less than 1 ppm.

With reference to step (h) of both procedures, the strongly polar solvent and/or hydrogenbonding solvent preferably has the following properties:

(i) It must be capable of dissolving polar compounds and asphaltenes of the types found or anticipated in the sample. As a general rule, a solvent or combination of solvents having a polarity between those of toluene and carbon disulfide will satisfy this requirement, and dichloromethane is a convenient and preferred solvent meeting this criterion.

(ii) It must be capable of displacing the most polar heavy oil molecules from the solid adsorbent material. The addition to the solvent of one or more alcohols miscible therewith provides this property, and when the solvent is based on dichloromethane, a convenient and preferred alcohol is isopropanol in volume concentrations in the range of from 1 to 50%, e.g., 10 vol% or thereabouts.

(iii) If ultraviolet spectroscopic analysis is employed for mass detection, as explained herein, the solvent (or combination solvent) must be transparent to UV radiation in the wavelength range employed.

(iv) If a mass detection step is used (e.g., gravimetric, flame ionization, inter alia) in which the removal of the solvent is necessary, the solvent must be relatively volatile for easy separation of solvent-free eluent, and the solvent must not associate too strongly with polar molecules in the eluent.

The monitoring of eluents in either chromatographic Method A or B is effected by UV absorption employing UV of selected wavelength(s), and the solvents used to produce the eluents are preferably transparent to UV of the selected wavelength(s). A highly significant benefit of employing UV absorption to monitor the eluents is that it can be employed for the accurate determination of the mass of aromatic carbon therein, as described hereinbelow.

A further object of this invention is to provide an improved method to detect the aromatic core content of separated fractions of aromatic containing feed, intermediate, and process streams. Such separations may be performed to purify or enrich a fraction with specifically desired aromatic structures. For example, such separations include distillation, extraction, and chromatography.

In the practice of liquid chromatography, it is difficult to use ultraviolet spectroscopy to quantify the level of aromatic cores in each eluted fraction due to the widely variant extinction coefficients for differently aromatic structures, as described above.

A common practice which only partially overcomes this difficulty is chromatographically separating the mixture of aromatics into classes of related molecules, such as those having the same number of rings, monitoring and integrating the absorbance at some wavelength or small number of wavelengths over time as each class elutes, and relating the integrated absorbance to the mass or concentration of eluted aromatic by a "response factor". The difficulty is that the extinction coefficient can be widely variant even within a class, as can be seen, for example, by relating the extinction coefficient for naphthalene to that of biphenyl or of phenanthrene to that of anthracene. As a result, different types of mixtures, such as hydrocarbon oils that come from different sources or have been processed differently, have different response factors. It is necessary to trap and weigh each chromatographically separated class and relate that to the measured integrated absorbance to obtain the response factors. This negates the advantage of having an automatic and rapid chromatographic determination of the composition of the mixture. It also limits the accuracy of the analysis, since small changes in processing may affect the response factors in unknown ways.

To overcome this difficulty, the integrated oscillator strength Q, as described in equation 1 above, was measured on chromatographically separated fractions of a series of known model compounds. The chromatography was high performance liquid chromatography, using Method A above. The eluent stream was directed through a flow cell and the full ultraviolet spectrum was measured every 3 seconds using a commercially available diode array spectrophotometer (HP 8451A). The absorbance was measured as a function of wavelength over the range 200 to 400 nm and converted to absorbance as a function of energy. The individual $Q(\lambda)$ results measured at every 2 nm from 200 to 400 nm were summed to provide the integrated oscillator strength Q from 200 to 400 nm.

The integrated oscillator strength was further integrated over time as the chromatograph developed. This result is multiplied by an appropriate constant to account for light pathlength, integration time, etc. The time integral of Q over the period corresponding to the elution of a compound was closely related to the moles of aromatic carbon atoms which elute regardless of the number of rings or substitution with alkyl groups, thiorings, or polar functional groups. This is shown in Table III.

TABLE III

Experimental Oscillator Strengths for Model Compounds Eluting in HPLC

| Compound | Experimental Oscillator Strength/mole ($\times 10^{-8}$) | Experimental Oscillator Strength/Moles Aromatic Carbon ($\times 10^{-8}$) |
| --- | --- | --- |
| 1 Ring Aromatics | | |
| Toluene | .91 | .151 ± 0.26 |
| Indan | 1.50 | .25 |
| Furan | .62 | .15 |
| Thiophene | .48 | .12 |
| Tetralin | 2.08 | .35 |
| Octahydroanthracene | 4.04 | .67 |
| Dodecahydrotriphenylene | 6.20 | 1.03 |

TABLE III-continued

Experimental Oscillator Strengths for Model Compounds Eluting in HPLC

| Compound | Experimental Oscillator Strength/mole ($\times 10^{-8}$) | Experimental Oscillator Strength/Moles Aromatic Carbon ($\times 10^{-8}$) |
| --- | --- | --- |
| Styrene | 4.46 | .56 |
| Indene | 4.31 | .54 |
| 2 Ring Aromatics | | |
| Naphthalene | 8.53 | .85 ± .125 |
| 2-Ethylnaphthalene | 10.41 | 1.04 |
| Benzothiophene | 6.03 | 0.75 |
| 9, 10 Dihydroanthracene | 4.11 | 0.41 |
| 9, 10 Dihydrophenanthrene | 8.61 | 0.72 |
| 3 Ring Aromatics | | |
| Anthracene | 12.61 | .901 ± .080 |
| Phenanthrene | 11.34 | .81 |
| 1-methylphenanthrene | 12.86 | .92 |
| Dibenzothiophene | 10.60 | .88 |
| 4+ Ring Aromatics | | |
| 1, 2 Benzanthracene | 17.51 | .973 ± .071 |
| 1, 2 Benzodiphenylene sulfide | 15.68 | .98 |
| Pyrene | 13.23 | .83 |
| Triphenylene | 14.24 | .79 |
| Benz($\alpha$)pyrene | 21.68 | 1.08 |
| Benz(e)pyrene | 22.13 | 1.11 |
| Fluoranthrene | 15.53 | .97 |
| Polars - Including Some 5+ Ring Aromatics* | | |
| Carbazol | 4.72 | .39 |
| 1, 25, 6 Dibenzanthracene | 12.00 | .54 |
| Phenanthridine | 6.31 | .49 |

*Experimental Oscillator Strength Measured from 234-400 nm Only

As a result of the small variance of the integral of Q over the chromatographic peak with the type of aromatic compound, it is found that a single response factor or set of response factors applies to all types of hydrocarbon oils regardless of their source or state of processing.

The measured integrated oscillator strength (Q) on polar compounds is multiplied by a factor of about 2.0 (or the integrated oscillator strength is multiplied by a factor of about 2.0 before it is measured) to derive the aromatic carbon because a part of the spectral region cannot be measured due to solvent (e.g., dichloromethane) absorbance.

As further demonstration that the method described provides an accurate measurement of aromatic core, a series of petroleum feedstocks was analyzed by HPLC Method A with oscillator strength detection. The sum of the weight percent of aromatic core in each chromatographic fraction represents the aromaticity of the oil as measured by $^{13}$C-NMR (Nuclear Magnetic Resonance).

Figure 2:
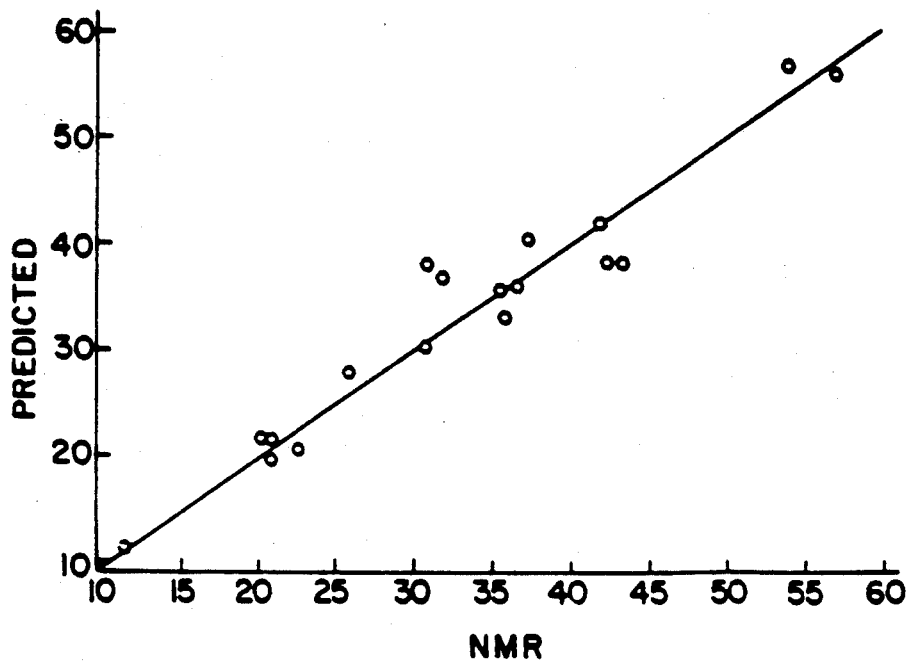
FIG. 2 is a regression-analysis graph of the weight percent of aromatic carbon in various hydrocarbon oil samples (6 virgin gas oils, 1 heavy coker gas oil, 5 deasphalted oils, 5 heavy Arab vacuum resid fractions, 4 resids) by NMR (on the abscissa) versus the predicted total aromatic core weight percent in the eluent as derived from chromatographic method A with integrated oscillator strength detection.

The results are shown on FIG. 2, which is a plot of percent carbon as aromatic carbon by NMR (abscissa) versus percent aromatic core as predicted by HPLC (ordinate). The HPLC aromaticity in this case was predicted as the sum of aromatic cores of molecules eluting as aromatics and 2.0 times the sum of aromatic cores of molecules eluting as polars.

The straight-line graph illustrating the linear correlation of the NMR values and the integrated oscillator strength values represents parity. The data fits the parity line even for oils of very different degree of saturated substitution, such as vacuum gas oils and coker gas oils, and oils of very different polar content, such as hydrotreated gas oils and vacuum residua. The theoretical basis for the independence of this quantity to aromatic type is not completely understood.

The total mass of components eluting from the column may be determined by, for example, differential refractometry, solvent evaporation followed by flame ionization of the oil, or solvent evaporation followed by light scattering off the remaining oil droplets. There are commercially available detectors for each of these procedures. Differential refractometry has the drawbacks that the refractive index of a component varies with its aromaticity and with the degree to which the saturated carbon is paraffinic or naphthenic. These drawbacks lead to the need to use feedstocktype-dependent response factors to relate the measured refractive index to the mass of component eluting. According to a preferred way of performing the invention, solvent evaporation followed by either flame ionization or light scattering is used to measure the total mass of oil components independently of the feedstock composition or the feedstock type. In the case of flame ionization, the particular instrument used (the flame ionization equipment described by J. B. Dixon of Tracor Instruments in paper No. 43 at the 1983 Pittsburgh Conference on Analytical Chemistry) has been found to cause some volatilization of lower boiling range oils along with the solvent evaporation, so it was most useful with vacuum distillation residua. In the case of light scattering, it is recognized that the light scattering response is a complicated function of the mass of solute eluting, and an appropriate calibration function must be derived. A recent publication (T. H. Mourey and L. E. Oppenheimer, Analytical Chemistry, 56: 2427–2434 (1984)) addresses the use of a light scattering detector for HPLC of polymers. For oil systems, this detector may be used to measure total component masses independently of feedstock type. The calibration functions are:

$$Mass = K_1 * (response)^x \quad (2)$$

where $x \leq 1$ at low response intensities; and $$Mass = K_2 * (response)^y \quad (3)$$

where $y \leq 1$ at high response intensities.
$K_1$ and $K_2$ are constants.

The combination of using one detector to measure aromatic core mass and another to measure total mass allows the saturated carbon substitution to be determined by difference (or ratio). This is a totally new concept in HPLC. Its validity has been established by comparisons of HPLC to mass spectroscopic analyses and by showing that the aromaticity of individual aromatic and polar components increases as expected during thermal treatment.

Figure 3:
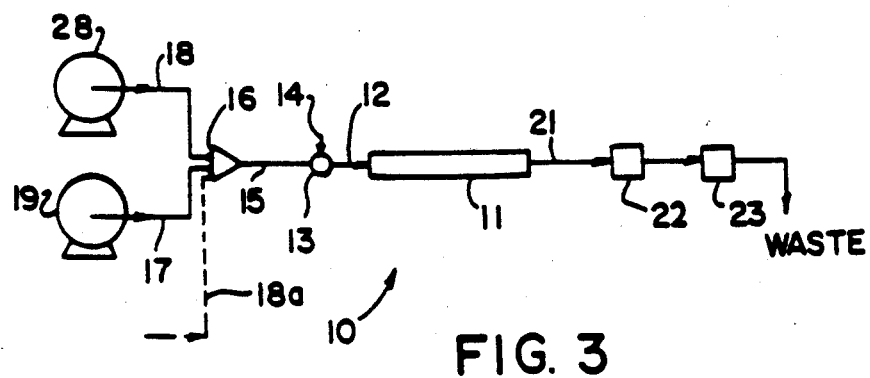
FIG. 3 is a schematic diagram showing one form of apparatus for use according to one way of performing the chromatographic method A of the invention.

Referring now to FIG. 3, the apparatus 10 comprises a chromatographic column 11 having an internal diameter of 4.6 mm and an overall length of 25 cm. The column is packed by the well-known slurry method with a commercially available stationary phase consisting of substantially fully $NH_2$-functionalized silica in finely divided form, having a mean particle size in the range suitable for high performance liquid chromatography (HPLC), e.g., 5 to 10 μm.

A conduit 12 extends from the upstream end of the column to a sample injection valve 13, and samples are injected into the valve 13 and conduit 12 from a sample injection line 14.

A solvent pipe 15 extends from the upstream end of the valve 13 to the downstream end of a solvent mixing chamber 16 which is connected to two solvent tubes 17, 18 to receive different solvents from respective suitable pumps 19, 20. The operations of the pumps 19, 20 are regulated by microprocessors (not shown). Each pump 19, 20 is connected to receive a respective solvent from a source thereof (not shown). A third pump may optionally be added or a single pump with proportioning inlet valves to different solvent reservoirs may be employed.

At the downstream end of the column 11, a conduit 21 conducts solvent(s) and eluents from the column to a variable wavelength ultraviolet detector 22 and thence to a mass-sensitive or mass-responsive detector 23 and thereafter to a sample disposal point and/or recovery and/or separation unit (not shown). The mass-sensitive or mass-responsive detector 23 may be a detector which monitors, or produces a signal in response to refractive index, flame ionization or light-scattering (after evaporation of solvent from the sample).

During the analysis, the microprocessor controllers regulate operation of the two pumps 19, 20 to maintain a substantially constant flow rate through column 11 of from 0.5 to 2.0 ml per minute. Initially, a weak solvent is employed which is substantially transparent to UV radiation and has a sufficient solubility parameter to dissolve all components of the sample to be introduced into the column but of which the solubility parameter is not so high that relatively sharp discrimination between different chemical types in the sample by HPLC will not be possible. The solubility parameter, delta, is the square root of the quotient of the energy of vaporization divided by its molecular volume (see C. A. Hansen et al, Encyclopedia of Chemical Technology by Kirk and Othmer, 2nd edition, Supplement, pages 889 to 910); i.e., delta $(E_v/V_m)^{0.5}$. The solubility parameter of the weak solvent should be in the range of from 7.6 to 8.8 cal$^{0.5}$cm$^{-1.5}$ and a preferred weak solvent is cyclohexane which dissolves all hydrocarbon components of hydrocarbon oil samples without causing precipitation of asphaltenes. Other weak solvents which may be used in place of cyclohexane are nonane, decane, dodecane, hexadecane, eicosane and methylcyclohexane, and combinations of at least two of the foregoing. Preferably, the solvent used is cyclohexane containing a trace proportion of a polar solvent in order to maintain the adsorption properties of the stationary phase at a constant value by deactiviating any residual silanol groups on the stationary phase. The preferred polar solvent for this purpose is an alcohol, particularly 2-propanol, and preferably a mixture of 99.99 volumes cyclohexane and 0.01 volumes 2-propanol is pumped by pump 19 to the column 11 during a first time period of operation.

During the first time period of operation, a sample of the hydrocarbon which is to be analyzed is passed via line 14 into injector valve 13 at a datum time where it co-mingles with the weak solvent from pump 19 to form a substantially uniform solution which is free of precipitated material such as asphaltenes. The magnitude of the sample is not critical within the limits which are conventional for high performance liquid chromatography, and a sample of 0.4 mg is usually satisfactory. The resulting solution passes into the upstream end of the column 11. In an alternative embodiment, a sample comprising a solution of the hydrocarbon in which the solvent is a weak solvent (conveniently but not necessarily the same solvent as is delivered by the pump 19) is introduced through injector valve 13 as a "slug" which is propelled through the column by further weak solvent from pump 19.

The liquid which emerges from the downstream end of the column 11 is constantly monitored in UV detector 22 and mass-sensitive detector 23. The UV-monitoring detector 22 and mass-sensitive detector 23 operate by the principles described herein. The response of these detectors may be digitized and automatically converted into levels or proportions of the various components in the oil sample.

The response in the mass-sensitive detector will typically start before the absorption of UV is detected due to the lower retentivity of saturated hydrocarbons than aromatics by the stationary packing material in the column 11 and will tend to overlap in time the UV absorption period as some aromatic hydrocarbon molecules pass through the UV detector at the same time as more diffusive aromatic molecules are passing through the mass-sensitive detector.

The diffusivity or rate of elution of molecules containing aromatic rings, as manifested by their rate of passage through the column 11, depends to a major extent on the number of aromatic rings in the molecules. Molecules having a single aromatic ring are eluted relatively rapidly while molecule containing two or more aromatic rings are eluted more slowly. Thus, by calibrating the column 11 with molecules containing different numbers of aromatic rings, it is possible to characterize eluted molecules in accordance with the time they have taken to pass through the column 11. Calibration is suitably effected with, e.g., toluene (one aromatic ring), anthracene (three condensed aromatic rings) and coronene (six condensed aromatic rings). The calibration may be effected with additional multi-ring compounds and/or different multi-ring compounds.

During operation of the method as disclosed herein, substantially all single-aromatic molecules will elute within a time span comparable with that of toluene, three-ring molecules will elute within a time span comparable with that of anthracene after the time span of the single-aromatic molecules, and six-aromatic ring compounds will elute after the time span of anthracene during a time span comparable with that of coronene. Molecules having numbers of aromatic rings between those of toluene and anthracene and between anthracene and coronene will elute after time periods between the respective pairs of molecules used for the calibration.

When substantially all the saturated and aromatic hydrocarbon molecules have been eluted from the column 11 by the weak solvent, as evidenced by a decline in the UV absorption and refractive index to virtually their base values with the solvent only, a strong solvent (i.e., a solvent having relatively high polarity) is passed into the column by pump 20 at a progressively increasing rate while the weak solvent is pumped by pump 19 at a corresponding progressively reducing rate so that the total volume-rate of solvent is substantially unaltered. After a selected third time period, the weak solvent is totally absent and the only solvent passing to the upstream end of the column 11 is the strong solvent. The strong solvent has a solubility parameter in the range of from 8.9 to 10.0 $cal^{0.5}/cm^{1.5}$ and is transparent to UV. A suitable strong solvent must be transparent to UV radiation at as low a wavelength as possible to facilitate calculation of the oscillator strength. The strong solvent must have a polarity between those of toluene and carbon disulfide, and is suitably dichloromethane. The dichloromethane may contain an alcohol in order to enhance its ability to elute polar high molecular weight molecules. Suitably, the alcohol is 2-propanol, and the strong solvent may consist of 90 vol% dichloromethane and 10 vol% 2-propanol. In a modification of the apparatus of FIG. 2 as so far described, pumps 19 and 20 may be employed respectively for passing the weak and strong solvents (e.g., cyclohexane and dichloromethane) via respective tubes 17 and 18 into the mixing chamber 16, and there may be an additional tube 18a for conducting the alochol or other high polarity eluting material from a respective third pump (not shown) to the mixing chamber 16. The third pump is preferably microprocessor controlled in relation to pumps 19 and 20 according to a predetermined sequence or program in a manner which is known in the art.

If the alcohol or other highly polar solvent modifier has not been introduced with the strong solvent in the third time period, it is introduced over a fourth time period (e.g., of five minutes or thereabouts). In either case, the alochol or other highly polar solvent modifier is introduced in steadily increasing rate with a correspondingly reducing rate for the strong solvent.

The modified strong solvent only is passed into the column 11 for a fifth time period to elute highly polar molecules from the column. The elution of polar molecules is detected by both detectors. The polar molecules of a typical hydrocarbon sample which contains asphaltenes are virtually completely eluted within a fifth time period of about 10 minutes, according to the relatively rapid decline in UV absorption after 3 to 10 minutes from the time when strong modified solvent only is pumped into the column.

When the elution of polar molecules is substantially completed, the strong solvent is progressively replaced by the weak solvent (i.e., 99.99 vol% cyclohexane with 0.01 vol% 2-propanol) over a sixth time period. Suitably, the sixth time period can be in the range from 1 to 10 minutes.

The weak solvent may be replaced by first interrupting the addition of the alcohol modifier to the strong solvent and then by progressively replacing the strong solvent by the weak solvent. The next hydrocarbon sample may then be passed into the column from injector valve 13 with weak solvent.

Reference is now made to FIG. 3 which refers to Method A in which the upper graph 30 shows the variation with time of the response of the material passing through the mass-sensitive evaporative light-scattering detector 23; and the lower graph 31 shows the variation with time of the UV oscillator strength of the material passing through the UV detector 22.

On the abscissa, the time is given in 3-second intervals or increments (hereinafter termed "channels" from time to time) from a datum time '0' which is 40 channels after the sample is injected.

The sample was 0.4 mg of heavy Arab vacuum residuum. The solvents were pumped by pumps 19, 20 either together in progressively changing proportions or individually to provide a constant solvent flow rate through the column 11 of 1.0 ml per minute.

In the initial time interval preceding the datum time, weak solvent only was passed from the pump 19 at the aforesaid rate of 1.0 ml/minute, and the light-scattering signal and UV oscillator strength were at constant levels during this time interval. The weak solvent alone was delivered by pump 19 through injector valve 13 for 7 minutes, from the time of injection of the hydrocarbon oil sample. Immediately thereafter, the strong solvent was progressively substituted for the weak solvent at a uniform rate (i.e., linearly over a period of 2 minutes). The strong solvent alone was then delivered by pump 19 through injector valve 20 for a period of 4.0 minutes, at which time it was progressively replaced over a period of 0.1 minutes by the modified strong solvent whose flow was thereafter maintained for a period of 12.9 minutes. In each case, a time lag arises, from the time of passing through the injection valve 13, for the sample or each solvent to reach the column and pass through it.

At the datum time, 40 channels, the 0.4 mg sample of vacuum residuum was injected from sample injection line 14 into injection valve 13. Due to the time lag, for the first 40 channels thereafter neither detector showed any deviation from the steady baseline before sample injection. Eleven channels later, the light-scattering signal as detected by detector 23 showed changes which comprised a sharp increase in response from the baseline 32 to a maximum point (point 33) followed by a progressive decrease towards the solvent-only value, interrupted at intervals by one or more increases in response. The light-scattering signal responded to the elution of 40 micrograms of benz(alpha)anthracene which was included as an internal standard, and indicated by peak 34. The elution of polar heteroaromatic species due to a solvent change to dichloromethane was indicated by peak 35, and the elution of strongly polar heteroaromatic species due to a change in solvent to 90% dichloromethane, 10% isopropanol was indicated by peak 36.

With reference to the UV oscillator strength graph 31, it will be observed that an increase in absorbance from the baseline began at about 15 channels and attained a peak (point 37) at about 24 channels. The peak value of absorbance was maintained for a short time and thereafter maintained a height above the baseline indicative of the aromatics eluting at each particular time. At point 38, the response of the internal standard is apparent. At 219 channels, corresponding approximately with the time of complete substitution of strong solvent for weak solvent in the column, there was a steep rise in UV absorbance which rose to a peak (point 39) due to polar compounds and thereafter exhibited a relatively rapid decline. The small additional peak 40 represents elution of highly polar compounds in the strong solvent.

When the strong solvent, dichloromethane, was modified in the column by the addition of 10 vol% isopropanol, the additional peak was observed and recorded. Finally, the detector response returned to a value very close to its initial baseline at point 42, at which time data collecting was ceased.

The relationship of the variations in light-scattering response and UV oscillator strength with solvent type is as follows: the initial change in light scattering corresponds with the elution of saturated hydrocarbons and a small proportion of aromatic hydrocarbons. The saturated hydrocarbons cause the peak at point 33, and the decline in light scattering thereafter is indicative of the relatively complete elution of saturates and an associated contribution from eluted aromatics. The relatively abrupt rise in UV absorbance leading to point 37 is attributed to the elution of aromatic hydrocarbons in the weak solvent. Aromatic species having progressively increasing numbers of rings, as shown in part by the internal standard, continue to elute from the column with weak solvent. The steep rise in UV absorption which commences shortly after the start of the progressive change from weak to strong solvent and which culminates in the peak absorbance (point 39) after the composition of the moving phase has changed to strong solvent only is attributed to the elution of polar compounds. Polar compounds are eluted relatively rapidly and efficiently (having regard to their relatively high molecular weights and physico-chemical properties) by the strong solvent until they are substantially wholly removed from the column.

The elution of highly polar substances, evidenced by peaks 40 and 41, leads to complete recovery of the oil which was injected into the column.

During the succeeding 34 minutes while the stationary phase in the column is subjected to equilibration with weak solvent (i.e., from 22 minutes to 60 minutes from the instant of sample introduction), the initial properties of the stationary phase are regenerated and a second cycle of analysis can be implemented by injecting the next sample. Thus, the overall cycle time is 60 minutes. The overall cycle time may be reduced by increasing the flow rate of solvents through the column and/or by starting the introduction of the strong and modified strong solvents at earlier times.

The proportions of each hydrocarbon type or component in a sample are obtained by converting the light-scattering response to a linear function of total mass, and the UV oscillator strength to a function of the mass of aromatic carbon, as described herein, and integrating each over a retention time interval. Components are defined by retention time intervals. Thus, saturates may be defined, determined or considered as those compounds eluting in the range between 9 and 16 channels, single-ring aromatics as those compounds eluting in the range from 16 to 24 channels, 2-ring aromatics as those eluting at from 24 to 40 channels, 3-ring aromatics as those eluting at from 40 to 75 channels, 4-ring aromatics as those eluting at from 75 to 200 channels, weak polar components as those eluting at from 200 to 300 channels, and strong polar components as those eluting at from 300 to 400 channels. The use of the model compounds to define the components is described herein.

The quality of a column is measured by chromatographing a "cocktail" containing toluene, anthracene, and coronene in cyclohexane. The column is run isocratically with cyclohexane and 0.01% 2-propanol. The capacity factors are 0.1, 0.5, and 2.0 for toluene, anthracene, and coronene, respectively, where the capacity factor is the quantity retention volume minus void volume divided by the void volume of the stationary packing phase in the column 11. Chromatography of this mixture is found to give a good indication of the quality of the column. If a column is contaminated with retained polars, or excessively aged, the capacity factors increase. It is also found that columns from different manufacturers disply widely different capacity factor and separation performances, even though they are all nominally $NH_2$ bonded silica. A summary of capacity factor data for different sources of adsorbent is given in Table IV. Columns with capacity factors for coronene greater than 5 gave poor separations due to low yields of aromatics and polar components.

TABLE IV

| CAPACITY FACTORS, R[1] FOR $NH_2$ FUNCTIONALIZED SILICAS | | | |
|---|---|---|---|
| Absorbent | Toluene | Anthracene | Coronene |
| Merck "Lichrosorb $NH_2$" | 0.1 | 0.5 | 2.0 |
| Merck "Lichrosorb $NH_2$" (aged)[2] | 0.1 | 0.6 | 4.3 |

TABLE IV-continued

CAPACITY FACTORS, R$^{(1)}$ FOR NH$_2$ FUNCTIONALIZED SILICAS

| Absorbent | Toluene | Anthracene | Coronene |
|---|---|---|---|
| Merck "Lichroprep NH$_2$" | 0.1 | 0.7 | 2.7 |
| DuPont "Zorbax NH$_2$"$^{(3)}$ | 0.35 | 2.9 | >11 |
| Waters "Energy Analysis Column" | 0.2 | 0.9 | 5.4 |

Notes:
Retention Volume - Void Volume
(1) R equals Void Volume
(2) Aged column was run with 50 cycles at semi-preparative scale loading (4 mg).
(3) Coronene elution required 40% strong solvent.

The separation achieved with cyclic semi-preparative scale use of this procedure shows good selectivity for micro-Conradson carbon residue (MCR), which is a measure of the coke forming tendency, and excellent selectivity for metalloporphyrins.

In a practical test of the method as disclosed herein, Cold Lake bitumen was separated into 65% non-polars (saturates and aromatics) showing a MCR of 2.7 and 37% polars with a MCR of 34 wt%. The whole bitumen had a MCR of 14.3 wt%. Heavy Arabian Vacuum Resid was separated into a non-polar fraction of 53%–58% with a MCR of 9 and a polar fraction with yield of 43%–47% and a MCR of 45%–47%. The whole resid had a MCR of 23 wt%. There were no metalloporphyrins detectable by visible spectroscopy ($\leq 1$ ppm) in the non-polar fractions. These data indicate that the refractory components (i.e., materials which are considered to be detrimental to the quality of a hydrocarbon sample and/or which adversely affect its subsequent usage) are concentrated in the polars fraction and that a high yield, selective separation of non-polars and polars has been achieved. The procedure retains aromatics as a function of their degree of conjugation. In all analyses using the methods and equipment of the invention, 99+% of the saturates, aromatics, polar molecules and asphaltene fractions is recovered within a relatively short analysis cycle (e.g., 30 minutes). This contrasts with open column such as those used in pursuance of ASTM D-4003 prior methods in which sample recovery is incomplete, typically about 95% and wherein the analysis requires relatively large samples (e.g., of the order of 3 grams) and a relatively long sampling time (e.g., about 8 hours).

The regenerability of the stationary phase has been amply demonstrated in practical tests. Individual columns 11 have each been used for well over 100 analytical cycles with 4 mg loadings before any significant loss of performance has been observed. The chromatographic method and equipment herein described can readily be adapted to operate automatically. The complete analytical sequence as described by way of non-limitative example with reference to FIGS. 2 and 3 takes 30 minutes, although it can obviously take a different time, and within the overall time of each cycle, the operation of the pumps for the weak and strong solvents, the timing of the injection of the oil sample and the recording of UV absorption data (and mass detector data, if required) can all be controlled by automatic sequencing equipment. Since such automatic sequencing equipment is well known in the art and readily available from commercial manufacturers, and, moreover, since it does not form a direct part of the invention but only a conventional item of equipment, no description thereof will be furnished herein.

The chromatographic method and equipment herein described can be employed for the evaluation of a hydrocarbon mixture or in the regulation or optimization of processes for refining or upgrading a hydrocarbon feed, for example in the fractional distillation of hydrocarbon feeds, in the preparation of feeds for catalytic cracking wherein at least a portion of the feed is subjected to catalytic hydrogenation to reduce its refractory nature, and in solvent refining (e.g., deasphalting) of hydrocarbon mixtures, inter alia.

Figure 6:
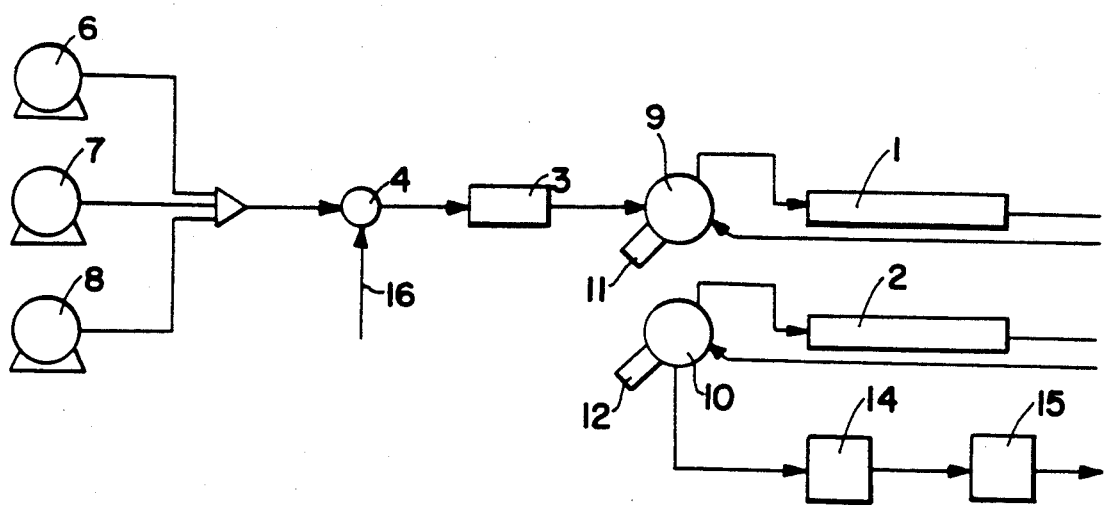
FIG. 6 is a schematic diagram showing one form of apparatus for use according to one way of performing the chromatographic method B of the invention.

Referring now to FIG. 6 which refers to Method B, the apparatus comprises two chromatographic columns [(1), (2)] each connected with narrow bore tubing to a separate six-port switching valve. Both columns have an internal diameter of 4.6 mm and an overall length of 25 cm. Each column is packed by the well-known slurry method with commercially available stationary phases.

The first column (1) is packed with a stationary phase consisting of substantially fully dinitroanilinopropyl-functionalized (DNAP) silica in a finely divided form, having a mean particle size in the range suitable for high performance liquid chromatography (HPLC), e.g., 5 to 10 microns.

The second column (2) is packed with a stationary phase consisting of a like finely divided HPLC grade silica partially functionalized with amine and cyano functionalities in a 2:1 ratio.

Narrow bore tubing extends from the upstream end of the column to a 0.5 micron filter (3) and further upstream to a sample injection valve (4). Samples are loaded into the valve (4) from a sample injection line (16).

Narrow bore tubing extends from the upstream end of the injection valve to the downstream end of a solvent mixing chamber (5) which receives up to three different solvents from respective suitable pumps (6), (7).and (8). The operation of the pumps is regulated by microprocessors (not shown). Each pump (6), (7) or (8) is connected to receive a respective solvent from a source thereof (not shown). A single pump with proportionation inlet valves to the different solvent reservoirs may be employed.

Figure 7A:
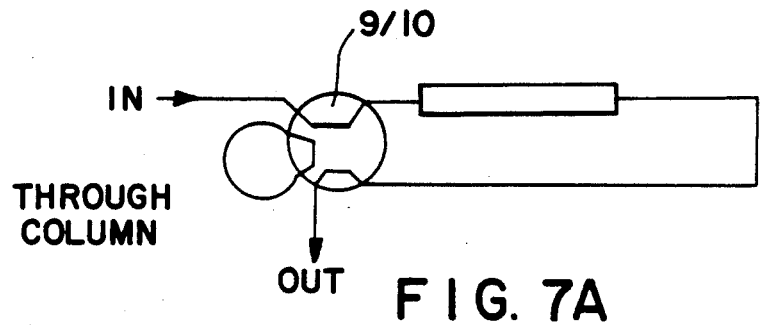
FIG. 7 is a schematic showing the switching valve arrangements which control flow in FIG. 6.
Figure 7B:
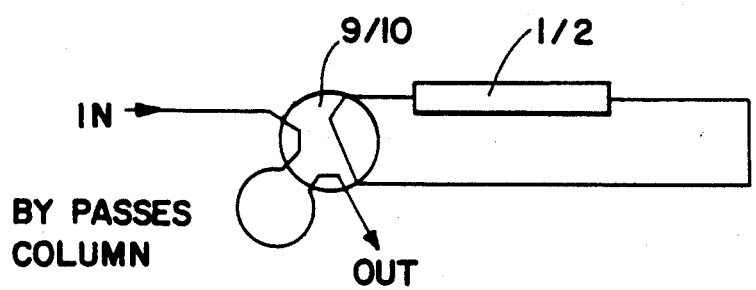

As shown in FIG. 7, the valves controlling the solvent flow to the columns (9) and (10) are configured so that the solvent flow may be directed through the column and then via narrow bore tubing back through the valve to the outlet port or upon switching the flow is directed through a short piece of tubing (11) or (12) directly to the outlet port. The position of each valve is controlled by microprocessors (not shown).

Narrow bore tubing connects the outlet of the second valve (10) to a variable wavelength ultraviolet detector (14) and thenceforth to a mass sensitive or mass responsive detector (15) and thereafter to a sample disposal point and/or recovery and/or separation unit (not shown). The mass-sensitive or mass responsive detector may be a detector which monitors or produces a signal in response to the refractive index, flame ionization or light scattering (after evaporation of the solvent from the sample).

To prepare a sample for analysis, the sample should be dissolved in a solvent which is substantially transparent to UV radiation and has sufficient solubility parameter to dissolve all components of the sample to be introduced into the columns but of which the solubility parameter is not so high as to perturb the relatively sharp discrimination between the saturates and monoaromatics in the initial stages of the separation. The solubility parameter of the weak solvent should be in the range of 7.6 to 8.8 cal$^{0.5}$/cm$^{1.5}$ and the preferred weak solvent is cyclohexane which dissolves all hydrocarbon components of hydrocarbon oil samples without causing the precipitation of asphaltenes. Other weak solvents that can be used in place of cyclohexane are nonane, decane, dodecane, hexadecane, methylcyclohexane, and decalin and combinations of at least two of the foregoing.

During the analysis, the microprocessor controllers regulate the operation of the pump(s) [(6), (7), (8)] to maintain a substantially constant flow rate of solvent through the columns (1) and/or (2) of from 0.5 to 2.5 ml per minute.

Initially, a weak solvent is employed which is substantially free of mositure, transparent to UV radiation, and has a solubility parameter sufficiently low to maintain the relatively sharp discrimination between different chemical types in the sample by HPLC. The solubility parameter of this weak solvent should be in the range of 7.0 to 7.8 cal$^{.5}$/cm$^{1.5}$ and a preferred weak solvent is hexane which provides a sharp separation between saturates and monoaromatics. Other weak solvents which may be used include pentane, heptane and iso-octane. To provide this separation the columns must be protected from mositure. Traces of water are removed from these solvents by the addition of fully activated 4A molecular sieves to the solvent containers prior to use.

During the first time interval of operation, a sample of the hydrocarbon which is to be analzyed is passed via line (16) into the injector valve (4) at a datum time where it co-mingles with the weak solvent. The magnitude of the sample is not critical within the limits of which are normal for high performance liquid chromatography, and a sample of 0.4 mg is satisfactory. In an alternative embodiment, a sample comprising a solution of the hydrocarbon in a weak solvent (conveniently but not necessarily the same as that delivered by pump (6) is introduced through the injector valve (4). In either case, the contents of the injector valve are propelled as a "slug" through the filter onto the column by further weak solvent from pump (6).

If the sample contains any material that is incompatible with the weak solvent, it may precipitate at the introduction of that solvent and be deposited on the filter frit. As the separation progresses the solvent flow is maintained through the injection valve and filter frit. Asphaltenes precipitated by contact with the weak solvent are eventually carried onto the column when the solvent strength has increased sufficiently to solubilize and mobilize asphaltenes on the stationary phase. This deposition/dissolution phenomena does not detract from the resolution achieved in the separation.

The liquid which emerges from the outlet of the second switching valve, i.e., the system eluent, is constantly monitored in UV detector 14 and the mass-sensitive detector 15. The response of the detectors may be digitized and automatically converted into levels or proportions of the various components of the oil sample.

The response in the mass-sensitive detector will typically start before the absorption of UV is detected because the non-UV-absorbing saturates are less retained by the stationary phases in the system than the aromatic and polar functionalities. The mass detector response will tend to overlap the time interval of the UV absorption as some aromatic hydrocarbon molecules pass through the UV detector at the same time as different molecules are passing through the mass-sensitive detector.

The rate of elution of molecules containing aromatic rings through a stationary phase is dependent on the nature of the surface functionality, the number of fused aromatic rings, and the solvent strength.

In the column system described herein, the first column functions by a "charge-transfer" or "donor-acceptor" molecular interaction. In this type of interaction the surface is covered with an electron-deficient functionality which strongly attracts molecules that possess diffuse electron clouds or free bonding electrons. With such a mechanism, the first column (1) aggressively retains aromatics with at least two rings and polar electron donating polars while providing minimal retention of the saturates and monoaromatics which pass on to the second column (2) for resolution.

The separate elution of the 2, 3, and 4-ring aromatics as well as the polars from this charge transfer column is achieved by programmed changes in the solvent strength as described in earlier sections.

Also, in the column system described herein, the second column (2) is a strong adsorption column, typically a lightly passivated silica gel surface, that aggressively retains molecules bearing any polarity but with only limited group-type selectivity. This highly active surface is sensitive to moisture and can irreversibly adsorb some polar molecules thereby changing its characteristics and limiting the possibilities of regeneration. The separation uses the weak solvent to elute the saturates and monoaromatics over this surface to achieve separation.

By programming the microprocessor to control the flow of solvent mixtures through the columns and to adjust the solvent strength, the separation may be optimized to bunch compounds of similar molecular structure into discrete, quantifiable fractions. The separation described herein has been so optimized by the determination of the retention of model compounds composition (Table V).

During the operation of the method described herein, model compounds are used to identify the cut points between fractions substantially all the saturates elute within a time span starting at a time corresponding to the retention of cholestane until that of nonadecylbenzene which signals the onset of the monoaromatics. The split between 1 and 2-ring aromatics occurs at the retention corresponding the retention of dodecahydrotriphenylene, while that for the $\frac{2}{3}$ ring split occurs at the point for acenaphthylene. Substantially all the 3-ring aromatics are found in the time interval between the acenaphthylene and the point where phenanthrene is removed from the column but fluoranthene remains in the column. The 4-rings then elute until chrysene has cleared the column. Materials retained beyond chrysene, starting with 5-ring aromatics such as perylene, are classified as polars.

In the following description, "pump" refers to either a combination of three individual pumps or a single pump equipped with three proporitoning valves to allow solvent programming to be accomplished.

Figure 10A:
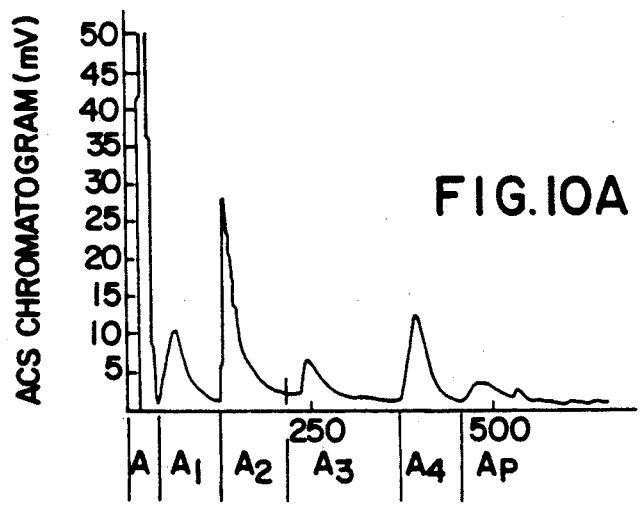
FIG. 10 shows two chromatographs relating to Method B.
Figure 10B:
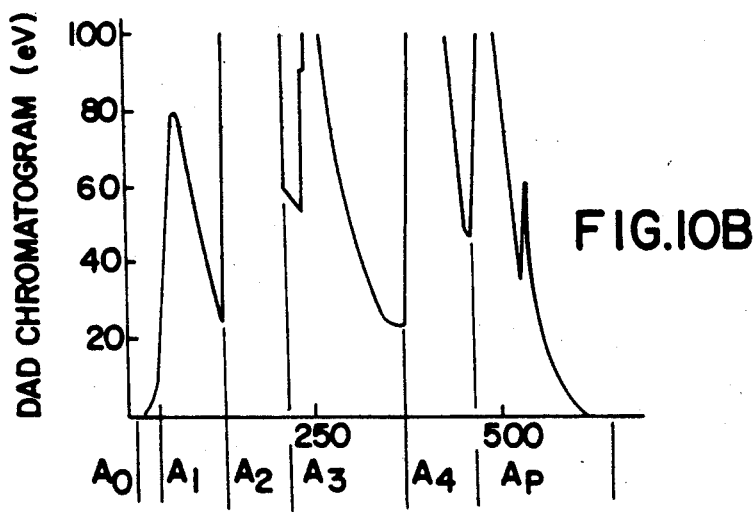

Reference is now made to FIG. 10 of the drawings in which FIG. 10a, the chromatogram (20), shows the variation with time of the response of the material passing through the mass-sensitive evaporative light-scattering detector; the chromatogram in FIG. 10b shows the variation with time of the UV oscillator strength of material passing through the UV detector.

On the abscissa, the time interval is given in three second intervals or increments (channels). Data is collected and plotted from a datum time "0" which occurs 180 seconds (60 channels) after the sample is injected.

The sample was 0.6 mg of a Heavy Arab lube extract. The solvents were pumped either together or in progressively changing proportions to provide a constant flow rate through the system of columns of 1.5 ml per minute.

In the initial time interval preceding the datum 0 time in the chromatogram, the weak solvent only was passed through the injection loop and both columns at the aforementioned rate of 1.5 ml per minute, and the light scattering signal and the UV oscillator strength were at constant levels during this time interval.

Three minutes after the injection, coincident with the initial datum 0, the solvent flow is diverted to bypass the charge transfer column while continuing to flow through the strong adsorption column. At 10 channels after the datum time 0 on the chromatogram, the light-scattering (mass-sensitive) detector shows a signal that rapidly rises from the baseline to a peak maximum (Ao) followed by a rapid decrease to a value close to the solvent-only value. This peak corresponds to the saturates present in the sample continues to a minimum at 34 channels.

While the pump continues to deliver the weak solvent, the monoaromatics (Al) are eluted leading to a response in the light-scattering mass detector that appears as the second peak (Al) in FIG. 10b. This elution continues with the mass detector response returning substantially to the solvent-only response prior to channel 125.

At channel 126, the chromatogram rises rapidly with the elution of the 2-ring aromatics. This occurs shortly after 9.6 minutes after injection the valves are switched simultaneously thereby returning the flow through the charge transfer column while bypassing the strong adsorption column. This initiates the elution of the 2-ring aromatics which rise almost immediately from channel 126 to a maximum (A2) then gradually drop in the direction of the solvent-only baseline to channel 210.

At 11.0 minutes, the solvent composition at the pump is changed by the introduction of an instantaneous step gradient to 5% of the strong solvent followed by a gradual reverse gradient to 2% strong solvent at 18 minutes. Thereupon, the strong solvent is increased in a 2 minute gradient to 25% followed by a 3 minute reverse gradient to 20% strong solvent at 23 minutes. This is followed by an increase to 90% strong solvent at 26 minutes. During the ensuing 3 minutes the composition of the solvent is modified by the replacement of 10% the weak solvent with 10% of the hydrogen bonding solvent. Finally, at 29 minutes a linear gradient is initiated that takes the composition to 25% hydrogen bonding solvent at 37 minutes.

In each solvent change, a time lag arises from the volume of the mixing system, the injection valve and the void volumes of the columns leading to solvent profiles which shows the 222 nm UV detector profile obtained with methylene chloride as the strong solvent. The initial 5% step, occurring at 11 minutes at the pump, arrives at this detector at channel 210. This corresponds to 13.5 minutes [(210 * 3 seconds)/60 seconds/minue + 3 minutes to datum 0] or a delay volume of 2.5 minutes.

The rise in the evaporative mass detector starting at 210 nm corresponds to the elution of 3-ring compounds initiated by the arrival of the strong solvent at the outlet of the active column, e.g., the charge transfer column (1). These 3-ring compounds continue to elute through a peak (A3) while the proportion of strong solvent that moves them is gradually decreased so that the minimum between the slowly eluted 3-ring compounds and the fastest 4-ring compounds is more clearly defined.

The onset of the 4-ring components (A4), initiated by the larger step in strong solvent, occurs at channel 376 and continues until channel 475 where the solvent strength is greatly increased. The elution of components with more than four fused aromatic rings or bearing polar heteroatomic functionalities are indicated by the increase in the response of the mass-sensitive light scattering detector leading to peak (AP). The components hydrogen bonding to the surface are displaced by the strong hydrogen bonding solvent that results in the "spike" that appears at channel 525 in the chromatogram. The substantially complete elution of the entire sample is indicated by the decrease of the light-scattering mass detector response to a value close to that of the solvent alone.

With reference to the UV oscillator strength chromatogram, it will be observed that the rise from the baseline begins at channel 17 and attains its maximum at about channel 64. (Despite the fact that the eluent passes through the UV detector first, its initial value occurs at a later channel than the mass detector because the saturates give no response in the UV detector; e.g., the first peak in the UV oscillator strength chromatogram corresponds to peak (Al) in the mass chromatogram.) The UV oscillator strength responding to the mixture of monoaromatics in this fraction then decreases slowly to the solvent-only value shortly before the valve switch at channel 125.

At channel 126, where the flow returns to the eluent coming from the charge-transfer column (1), the UV oscillator strength rises sharply corresponding to the elution of the di-aromatics in peak (A2) at 140 and drops in the direction of the solvent-only response.

At channel 210 (the end of the 2-ring aromatics), the precipitous drop in the UV oscillator strength chromatogram reflects a narrowing of energy range corresponding to 234 to 430 nm, thus allowing spectra of the 3-ring, 4-ring and polar fractions to be measured without interference from the strong solvent, methylene chloride. Model compound data demonstrates that there is a constant response in UV oscillator strength per aromatic carbon for all three of these classes over the energy range equivalent to these wavelengths.

Beyond the drop at channel 210, the peaks observed in UV oscillator chromatogram arise from the solvent strength changes heretofore described in the discussion of the mass detector chromatogram. Again, the return of the UV oscillator strength chromatogram to the solvent-only level demonstrates that polar compounds are eluted wholly and efficiently (having regard to their relatively high molecular weights and physico-chemical properties).

During the ensuring 38 minutes, the stationary phases of the two columns are subjected to equilibration with a reverse sequence of solvent strength so that the initial activity of the columns is regenerated and the system is ready for the injection of a subsequent analysis. Thus the overall cycle time for an analysis is about 75 minutes.

After the separation is complete, the regeneration sequence is initiated by eliminating the hydrogen bonding solvent and increasing the flow rate of the strong solvent. This strong solvent flow which passes through the charge transfer column (1) only is continued for a few minutes to sufficiently remove the hydrogen bonding solvent from its surface.

Subsequently, a 2 minute gradient is initiated that returns the solvent composition to 100% weak solvent. This flow of weak solvent is continued for six minutes, at which time the flow is redirected to include the strong adsorption column (2) by the switching valve. This flow is then continued to return to a fully activated system with both columns at their initial activity and with no residual strong solvent detectable in the UV oscillator strength measurement.

The flow is then returned to the initial flow rate. The overall cycle time may be reduced by increasing the flow rates of solvent through the column and by making compensating adjustments in the times at which the solvent and valve switching occurs. A limitation on this increase operation is the back-pressure that this may exert on the pumping system.

The proportions of each hydrocarbon type or component in a sample are obtained by converting the light scattering detector response to a linear function of total mass, the UV oscillator strength to a function of the mass of aromatic carbon, as described herein, and integrating each over a retention time interval.

Components are defined by the retention time interval, e.g., the channels for each type. Thus, saturates may be defined, determined or considered as those compounds eluting in the range between 10 and 34 channels, single ring aromatics as those compounds eluting in the range of 35 to 125 channels, 2-ring aromatics as those eluting from at channel 126 to channel 210, 3-ring aromatics as those eluting at channel 211 to 375, 4-ring aromatics as those eluting at channel 376 to 475, and polars as those components eluting at from channel 476 to the final channel 660.

The model compounds used to define these ranges has been mentioned previously. Substantial differences exist between different types of charge transfer and strong adsorption columns. To utilize this method, the valve switching times and solvent strength gradients must be adjusted to provide chromatofocusing of these models into convenient groups. Referring to the compounds in FIG. 10, the cut points between groups are established as follows:

The time for the initiation of data collection is set 10-15 channels earlier than the elution time of cholestane.

The time at which valve is to be switched to initiate the bypass of the charge transfer column valve is set at the retention time of dodecahydrotriphenylene when separated on that column with flow of the weak solvent.

The end time of the bypass of the charge transfer column is determined by the time necessary for the dodecahydrotriphenylene to pass through both the charge transfer column and the strong adsorption column when separated on both with flow of the weak solvent. This time is converted into the channel number for the start of the two ring aromatics by correcting for the time delay between the injection and the initial datum channel 0.

The end time for the 2-ring aromatics is determined as that time required for acenaphthylene to pass through the charge transfer column, including the time when the column has been bypassed by the valve switching, when separated flow of weak solvent. This time is converted into the end channel number for the 2-ring aromatic by correcting for the time delay between the injection and the initial datum channel 0. This channel N is the start of the 3-ring fraction; N-1 is the end of the 2-ring channel.

The solvent gradient to complete the removal of the 3-ring fraction is then developed by optimizing solvent strength so that the UV oscillator strength response approaches the solvent-only response in a clear minimum between phenanthrene and fluoranthene when co-injected. The retention time of the minimum is then converted to a channel value for the end of the 3-ring aromatics as previously described.

The next channel is the first for the 4-ring aromatics. The last channel for this range is established as in the preceeding paragraph except using the minimum between chrysene and perylene when co-injected. This minimum is converted as previously to the channel number for the end of the 4-rings.

TABLE V

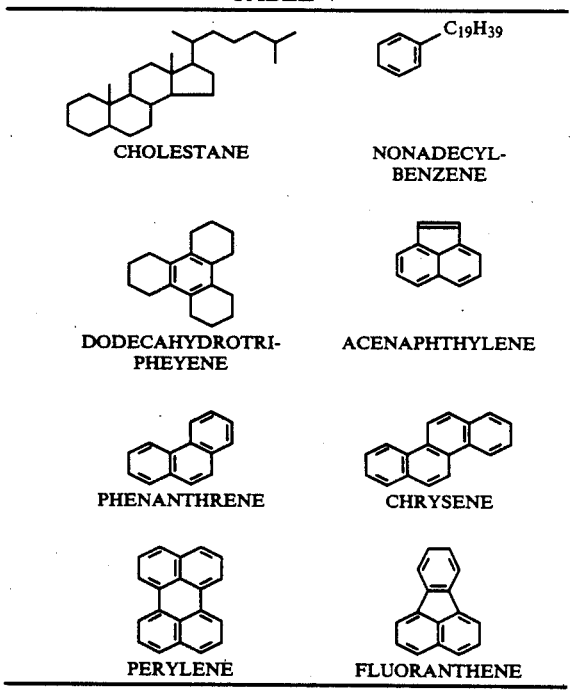

CHOLESTANE  NONADECYL-BENZENE

DODECAHYDROTRI-PHEYENE  ACENAPHTHYLENE

PHENANTHRENE  CHRYSENE

PERYLENE  FLUORANTHENE

The next channel is the first for the polars. The composition of the solvent mixture for this final fraction is optimized as the blend of strong and hydrogen bonding solvents that is sufficient to complete the elution of the polars in a vacuum resid as evidenced by the return to solvent-only response for both the UV oscillator strength and evaporative light-scattering mass detector.

Once the conditions for these polar fractions have been established, a regeneration profile is established to return the columns to their initial activity. This activity is characterized by the freedom of strong solvent interference in the measurement of UV oscillator strength and by a defined minimum between the saturates and the monoaromatics for a typical heavy vacuum gas oil.

Once the regeneration sequence has been established, the channels for the saturates and mono-aromatics is established by injecting a series of representative samples to be analyzed and finding the average retention channel for the initial rise of the response in the evaporative light scattering mass detector (start channel for saturates) and the average channel for the minimum between the saturates and monoaromatics (final saturates point). The point beyond the valley corresponds to the start of the monoaromatics.

Having established the channel points that distinguish between component ring types, a lube extract is run routinely as a functional quality control check.

COMPARATIVE EXAMPLE

In the article in J. Chromatography (1981) 206, 289-300, C. Bollet et al describe a high performance liquid chromatography technique that is said to be capable of analyzing a vacuum residue (boiling range above 535° C.) for saturates, aromatics, and polar compounds. The technique employs two procedures. In the first procedure, saturates are separated from aromatics and polars using a stationary phase of 10 micrometer silica-bonded alkylamine in a column 20 cm long by 4.8 mm internal diameter. The mobile phase used was n-hexane, and it is stated that for asphaltene-containing samples, cyclohexane should be used as the mobile phase to avoid precipitation of asphaltenes. The article does not state that there is complete recovery of the sample in the eluent, but the article could be interpreted as implying that there is in fact 100% sample recovery.

Figure 4A:
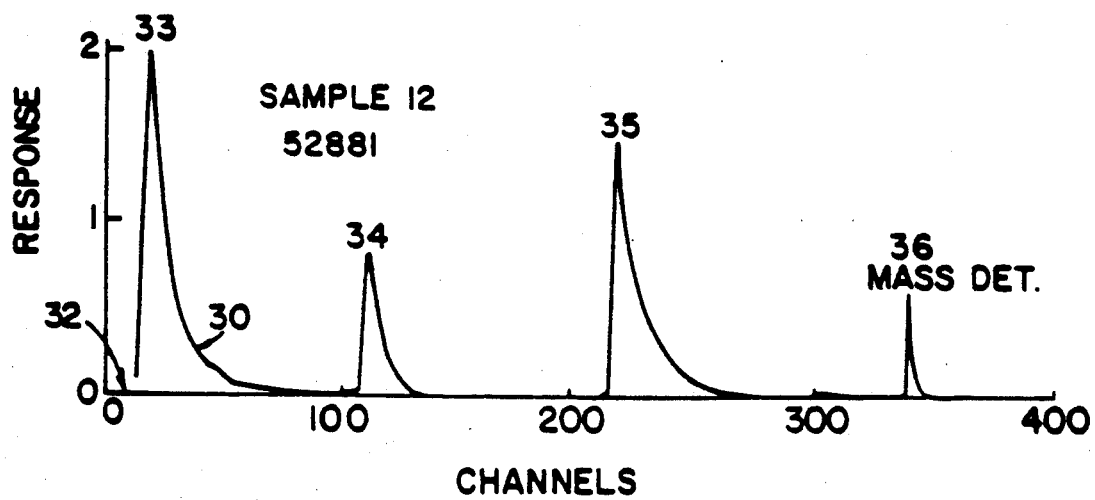
FIG. 4 is a graph showing compositional data on the ordinate versus time on the abscissa for an analysis carried out using the apparatus of FIG. 3.
Figure 4B:
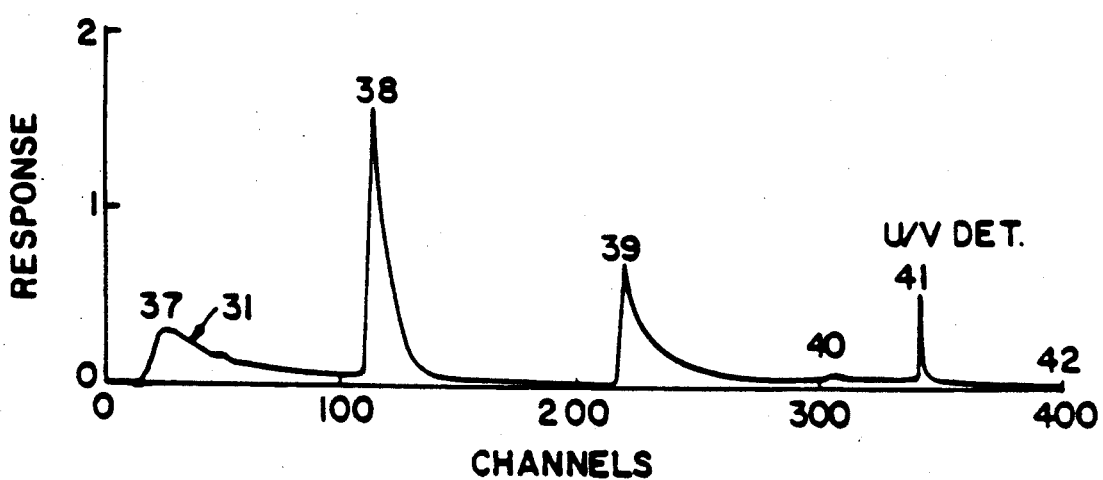

According to the second procedure of Bollet et al, in which separation of saturates together with aromatic compounds from polar compounds is carried out using a more polar solvent, a chromatographic column packed with Merck Lichrosorb-$NH_2$ functionalized silica was equilibrated with a solvent comprised of 85% cyclo-hexane and 15% chloroform at a flow rate of 2.0 ml/min. 120 microgram of an Arabian heavy vacuum distillation residue (950° F.+, 510° C.+) was injected into the column in 20 microliter of cyclohexane solution. Detection was by monitoring UV absorbance at 254, 280, and 330 nm. The chromatogram generated (at 280 nm) is shown in FIG. 4a and indicates the dilution of saturates and aromatics. The flow was then reversed (backflush). Polar compounds eluted over the next 10 minutes by which time a stable baseline was reached. This is shown in FIG. 4B (UV absorbance monitored at 280 nm). A sharp peak as reported by Bollet et al was not found. This completed the Bollet et al analysis.

The method described by Bollet et al was compared with the method disclosed herein and, as will be seen from the following results, the Bollet et al method leaves a considerable amount of the sample material, principally polar compounds, in the column, whereas 100% recovery (or essentially 100% recovery) is achieved by the present method.

To show that polars recovery was incomplete, and as an example of one way of performing the method of the invention, the flow was reversed to its normal (forward) direction and a solvent of 90% dichloromethane and 10% isopropanol was introduced in a solvent gradient over 10 minutes. The absorbance was measured for 20 minutes during which time an additional peak due to strongly retained polars emerged at about 8 minutes (FIG. 4, which shows the absorbance at 280 nm).

Figure 5A:
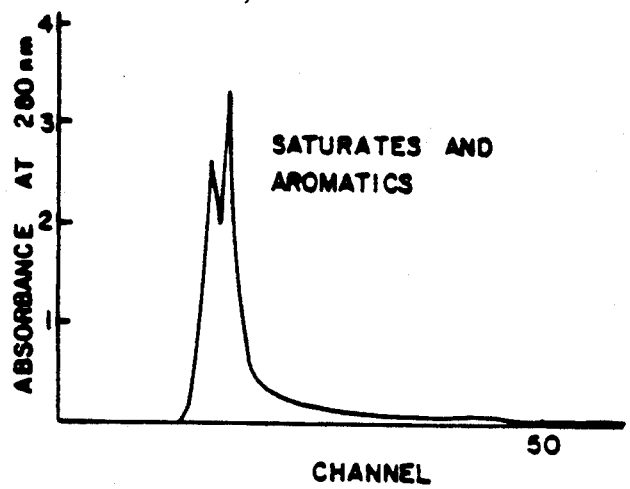
FIG. 5 shows in graphs (a) and (b) absorbance versus time of eluents recovered during a repetition of the method described by Bollet et al in J. Chromatography (1981), 206 289-300; and in (c) an additional step needed to obtain complete recovery.
Figure 5B:
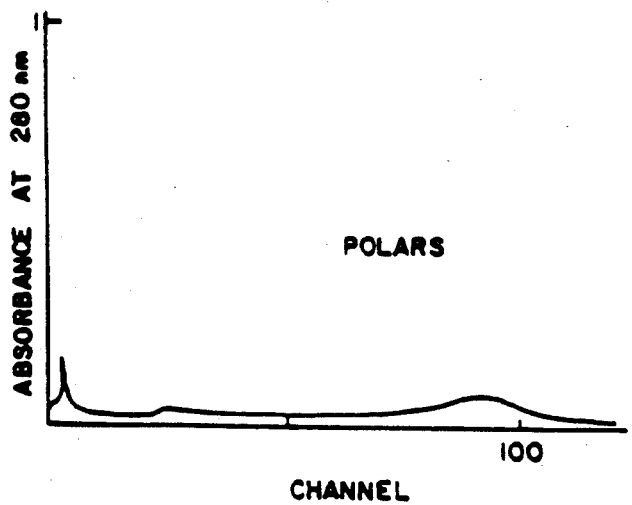
Figure 5C:
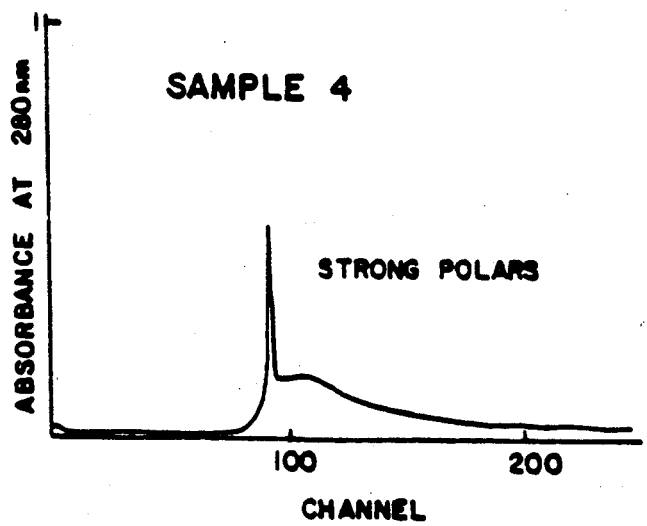

Thus, the Bollet et al method leaves some of the polar material on the column. The absorbance in each of FIGS. 5a to 5c was integrated over time to obtain a measure of how much material was removed from the column in each step. The results are:

|  | Normalized Area (%) |
|---|---|
| Forward Flow Cyclohexane: | |
| Chloroform (85:15) | 79.5 |
| -Eluent: Saturates and Aromatics | |
| Backflush Cyclohexane: | |
| Chloroform (85:15) | 8.4 |
| -Eluent: Polars | |
| Forward Flow Dichloromethane: | |
| Isopropanol (90:10) | 12.1 |
| -Eluent: Additional Polars | |

The amount of material which the Bollet et al method leaves on the column is about 12% of the vacuum residue sample. This creates several problems which are avoided or overcome by the method disclosed herein, namely:

The material left on the column is not properly accounted for in the compositional analysis.

The material left on the column creates adsorbing sites for subsequent analysis, giving irreproducible results.

The material left on the column can eventually block the flow, causing high back pressure and loss of operation.

In order to achieve good recovery of residual oils from an HPLC column, the solid adsorbent material must be functionalized to shield the inorganic oxides and hydroxyls. The final eluting solvent must display solubility for asphaltenes and have a hydrogen bonding functionality and/or other highly polar functionality to neutralize the surface polarity of the adsorbent. The preferred combination is to use primary amine-functionalized silica as the adsorbent and a mix of dichloromethane and isopropanol, where the isopropanol is present at volume concentrations in the range of from 1 to 50%, most preferably 10%, as the final solvent in the elution of the oil. This solvent may be introduced either in forward flow or backflush. It is the solubility and polarity aspects of the solvent which are important, not the flow direction.

In a modification of the separation, a three pump system is employed. The first pump delivers cyclohexane, the second dichloromethane, and the third isopropanol. The delivery rates are varied in time. Cyclohexane is used to elute saturates followed by aromatics, weakly polar compounds are then eluted with dichloromethane, and, finally, strongly polar molecules are eluted with 10% isopropanol in dichloromethane. The exact solvent composition program is not critical to obtaining information, since component assignments can be varied. It is important to increase the solubility parameter of the solvent as the chromatography proceeds, so that oil components of successively increasing solubility parameter can be desorbed and measured. Preferably, the solubility parameter of the solvent is increased progressively, rather than as a step change. However, a step change may be used and is within the scope of the present invention as defined by the appended claims.

The distinction of being able to accurately analyze residua is among the more important advantages which the method disclosed herein provides over the prior art. There are, however, several other advantages in the present method versus the prior art of Bollet et al, namely:

Only a one-step procedure is used instead of two procedures, making the present method simpler.

The aromatics are separated by their number of condensed aromatic rings, thus giving additional compositional information.

New detection schemes as described herein allow quantification of oil components without the need to obtain response factors for each compound type.

According to the invention from another aspect there is provided a process for refining or upgrading a petroleum hydrocarbon feed, in which samples of hydrocarbon oil produced in the process are each chromatographically analyzed by a method as defined above to determine the level present of at least one component in the oil, and in which the operation of the process is controlled in dependence upon the determined level present of said at least one component.

Usually but not necessarily the control of the operation of the process is such as to oppose any rise in value of the level present of said at least one component above a predetermined value.

The invention, according to a preferred application, provides a method of evaluating the quality of a hydrocarbon mixture comprising analyzing at least one sample of the hydrocarbon mixture by one of the chromatographic methods as herein described and thereby determining the proportions of species selected from at least one of the following: saturates, aromatics, polynuclear-aromatics, polar compounds, asphaltenes and a mixture comprising at least two of the foregoing. The hydrocarbon mixture may be a feedstock for a refining process or an intermediate processed oil between two refining steps. The evaluation performed by this preferred method of the invention enables the refining process or processes to be adjusted as necessary (within their permissible operating limits) to produce a product and/or intermediate product having a composition which matches or closely approximates to the optimum specification for the product and/or intermediate product.

The invention, in one application, also provides a process for refining or upgrading a petroleum hydrocarbon feed containing asphaltenic materials in which the feed is passed to a fractionation unit having a temperature and pressure gradient thereacross for separation into components according to the boiling ranges thereof, said components being recovered from respective regions of the fractionation unit and including a gas oil component boiling in a gas oil boiling range which is recovered from a gas oil recovery region of the unit, wherein discrete samples of gas oil fraction are taken from the recovered gas oil fraction at intervals and each analyzed by the method as herein described, and wherein a signal representative of the amount of asphaltenic material present in each sample is generated and employed to modulate the operation of the fractionation unit so that the amount of polar component in the gas oil component is maintained below a predetermined amount.

The invention, in another application, further provides a process for refining or upgrading a petroleum hydrocarbon feed (e.g., boiling in the gas oil boiling range) in which the feed is passed to a catalytic cracking unit and converted to cracked products including upgraded hydrocarbon materials, wherein discrete samples of the feed passing to the catalytic cracking unit are taken at intervals and each analyzed by the method as described herein, and a signal representative of the amounts of polar components and aromatic components having at least three rings ("3+ring aromatics") is generated, and the feed is either blended with a higher quality feed or subjected to a catalytic hydrogenation treatment or both blended and catalytically hydrogenated if and/or when said signal corresponds to amounts of 3+ ring aromatic components and polar components in excess of predetermined amounts, the amount of blending and/or the intensity of said catalytic hydrogenation treatment being increased and decreased with respective increases and decreases in the magnitude of the said signal.

The invention, in yet another application, also provides a process for refining and upgrading a petroleum hydrocarbon feed containing undesirable contaminating components selected from asphaltenic materials, aromatic components containing at least three conjugated aromatic rings ("3+aromatics"), polar components and mixtures of at least two of said contaminating components comprising the steps of mixing a stream of the hydrocarbon feed with a stream of a selective refining agent at selected refining conditions and separately recovering from the resulting mixture (i) a hydrocarbon raffinate stream having a reduced content of polar components and aromatic components; and (ii) a stream of a mixture containing solvent and at least one of said contaminating components, wherein discrete samples of the raffinate stream are taken at intervals and each analyzed by the method as herein described and wherein a signal representative of the amount of contaminating component is derived, the signal being employed directly or indirectly to vary or regulate the said refining conditions so as to maintain the amount of contaminating component in the raffinate below a selected amount.

In each one of the refining or upgrading processes hereinbefore mentioned (i.e., distillation, solvent refining and catalytic cracking or coking), the present chromatographic method and equipment may be used to detect unacceptable levels of a particular type of hydrocarbon or other material, and upon such detection, a signal is derived or produced from which the operation of the process, and/or a step associated with the process, may be modulated in order to reduce the level of the undesirable hydrocarbon or other material to below the unacceptable level. Thus, referring to each of the said foregoing processes in turn, the following are the principal objectives and the manner in which they are achieved pursuant to the invention.

1. Distillation

In the distillation of hydrocarbon feeds containing asphaltenic material (hereinafter termed "asphaltenes" for brevity), a number of factors can lead to an excessive amount of entrainment or carryover of asphaltenes into the distillate fractions, particularly the gas oil fractions. Such factors include, but are not limited to, excessive stripping steam rates; excessively high heat input to the bottom recycle streams; excessively high feed rate.

Since the presence of excessive asphaltenes in a distillate is usually detrimental to the quality of the distillate and/or its subsequent use, the utilization of the equipment and method disclosed herein to detect excessive asphaltenes represents an important step forward in optimizing the operation of a distillation column.

According to this aspect, 0.4 mg samples of gas oil from the distillation column at a suitable standardized temperature (e.g., 25° C.) are injected via valve 13 into the equipment of FIG. 3 and subjected to the chromatographic analysis described with reference to FIGS. 3 and 4. The asphaltenes are highly polar and their concentration in the gas oil sample can readily be ascertained from the area beneath the UV oscillator strength curve during elution with the strong solvent (e.g., between points 38 and 42 of FIG. 4). The area beneath the UV oscillator strength curve is determined in accordance with any of the well-known conventional techniques for so doing, and where the area is in excess of an acceptable area, any one or more of the known expedients to reduce asphaltene entrainment in the distillation tower may be implemented. Since it is not usually desirable to reduce the feed rate to the tower, the expedient which may be employed first is to reduce the rate of stripping steam. The reduction in heat input to the tower may be compensated for by increasing the temperature of the bottoms reflux temperature rather than the feed temperature to regulate asphaltenes carryover, as will be known to those skilled in this field. The regulation of the operation of the distillation tower in accordance with the asphaltenes as determined by the chromatographic method disclosed herein may be effected by manual adjustment, by operatives based on the output of the chromatograph, or automatically, also based on the output of the chromatograph.

2. Solvent Refining

In solvent refining, a feedstock is intimately contacted with a solvent having a selective solvency or affinity for a particular type of material in the feed and the resulting solution is separated from the remaining raffinate. In solvent deasphalting a feed containing asphaltenic materials, hereinafter termed asphaltenes for brevity, is mixed with a short chain n-paraffin, such as n-propane, which is completely miscible with non-asphaltenes but immiscible with asphaltenes whereby the latter form a second, heavier phase and can be removed by suitable separation techniques, e.g., decantation. If the deasphalting operation is performed at an excessively high rate for the separation of the asphaltene from the solvent-oil solution to occur in the available equipment, asphaltene will be entrained into the otherwise deasphalted solution.

In order to monitor the asphaltene content of the deasphalted solution, a sample of the latter is passed at a suitable standard temperature into chromatographic equipment of the type described with reference to FIG. 3, and the area under the UV oscillator strength curve during elution with strong solvent (corresponding to the area under curve 31 from points 38 to 40 in FIG. 4) is determined by any of the known techniques. If the area is in excess of the area representative of an acceptable amount of entrained asphaltenes, the feed rate is reduced either by manual intervention or automatically until an acceptable asphaltene entrainment level is attained.

3. Preparation of Catalytic Cracker Feeds (and/or Upgrading of Gas Oil)

Catalytic cracker feedstocks in particular, and gas oils in general, tend to contain proportions of molecules containing one or more aromatic rings and also polar molecules. The multi-aromatic molecules tend to resist cracking during their passage through a catalytic cracking unit and therefore tend to be concentrated in the cracked products, while polar molecules tend to decompose during cracking to give relatively large carbonaceous deposits on the catalyst, thereby impairing the catalytic activity of the latter. Moreover, gas oil and other fractions containing multi-ring aromatic structures tend to produce smoke on combustion, and, for at least the foregoing considerations, it is desirable to be able to control the levels of multi-aromatic molecules and polar molecules in gas oils and other hydrocarbon fractions.

One method by which the concentration of asphaltenes, resins and multi-aromatic ring molecules in a distillate fraction such as gas oil may be regulated is to control the cut-point of the fraction during distillation, and the method for doing this has already been described herein in relation to distillation. When the concentration of asphaltenes and multi-aromatic ring molecules in a distillate fraction from a distillation unit is found to be in excess of a desired maximum concentration using the chromatographic equipment and method as disclosed herein, signals representative of the UV-absorption characteristics of asphaltenes and multi-aromatic ring molecules and indicative of the excess concentrations thereof are derived and employed to control the operation of the distillation unit until the concentration of such molecules is reduced to an acceptable level in the distillate fraction.

In the context of catalytic cracking, one method of reducing the tendency of aromatic molecules (including multi-aromatic molecules) to be concentrated in the cracked products is to hydrogenate them since the resulting naphthenic structures (i.e., cycloparaffinic structures) crack relatively readily. Hydrogenation also tends to reduce the concentration of polar compounds. The hydrogenation is promoted by means of a suitable hydrogenation catalyst, e.g., a combination of metals from Groups VI and VII of the Periodic Table (e.g., Mo and Co) on a low-acid carrier such as alumina.

In relative terms, hydrogen is an expensive commodity and therefore it is highly desirable from the economics viewpoint to hydrogenate only that selected proportion of the hydrocarbon material whose hydrogenation will result in the production of cracked products of an acceptable quality. The proportion which is hydrogenated may be selected by diverting the desired proportion to a hydrogenating unit or passing all the feed through the hydrogenating unit and varying the hydrogenating conditions to effect the desired proportion of hydrogenation, or by a combination of both of the foregoing expedients in appropriate degrees. Generally speaking, the catalytic hydrotreatment of multi-aromatic molecules results in the hydrogenation of only one at a time of the aromatic rings in the molecules per hydrotreatment. The hydrogenated ring is cracked upon passage through the catalytic cracker and the resulting molecule with one less aromatic ring may be further hydrogenated to facilitate the cracking of an additional saturated aromatic ring upon each subsequent passage through the catalytic cracker until the content of refractory aromatic molecules in the cracked products is reduced to an acceptable level.

Catalytic hydrogenation of polar molecules is also practiced to the extent necessary to enhance the quality of the hydrocarbon fraction to a level suitable for its subsequent use, e.g., in catalytic cracking.

Figure 9:
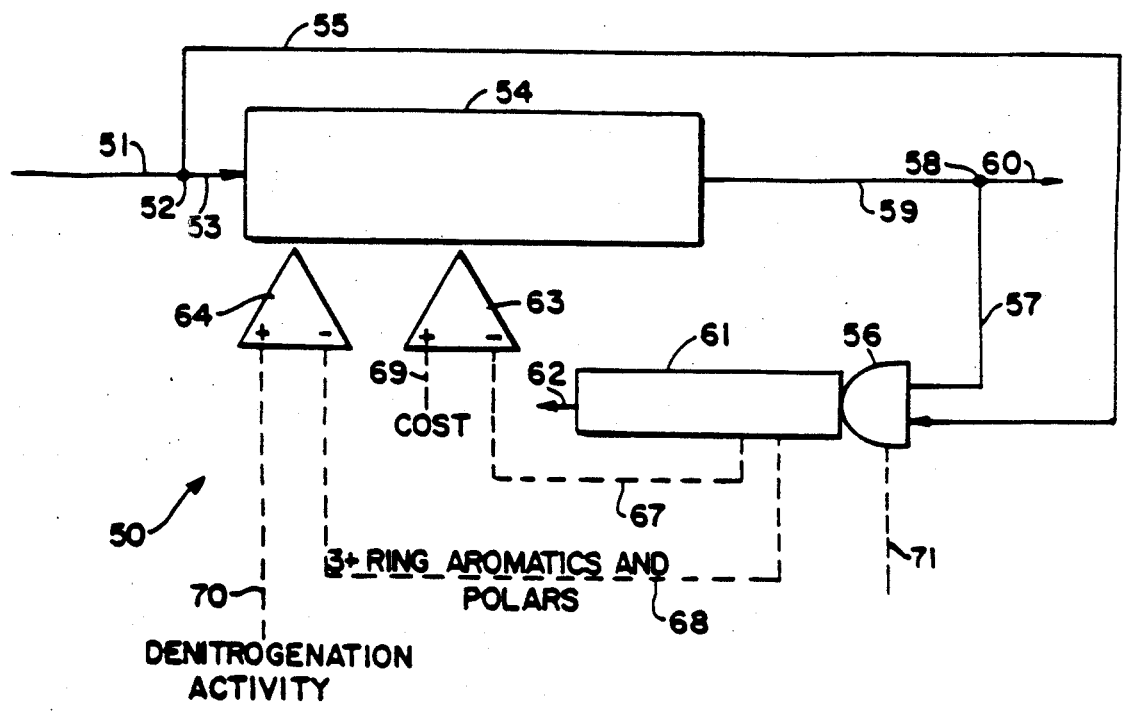
FIG. 9 is a chemical engineering flow sheet of a process and regulating equipment therefor, wherein the regulating equipment embodies apparatus for use according to one way of performing the method of the present invention.
Figure 8:
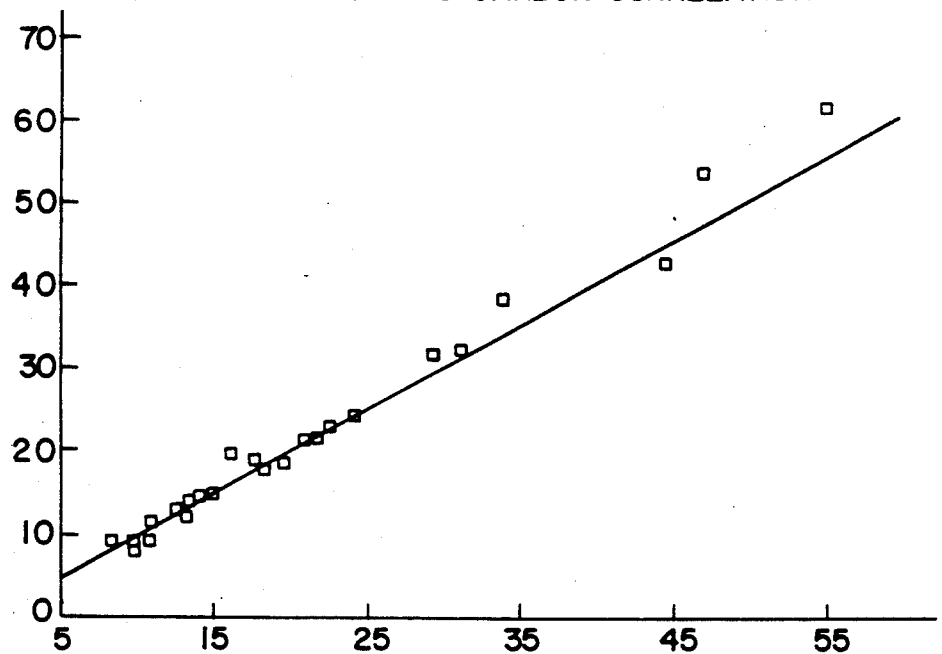
FIG. 8 is a graph of the weight percent of aromatic carbon in various hydrocarbon oil samples by $C_{13}$ NMR (on the abscissa) versus the predicted total aromatic core weight percent in the eluent as derived from chromatographic method B with integrated oscillation strength detection.

By way of example, reference is now made to FIG. 9 which shows, in a block chemical engineering flow diagram, the principal features of a catalytic hydrotreatment unit 50 embodying process control. In this nonlimitative example, the unit is for enhancing the quality of a catalytic cracker feedstock, but it will be appreciated by those skilled in the art that it can be used to enhance the quality of feedstocks for other purposes.

The unprocessed feed (e.g., a gas oil fraction from a vacuum distillation tower) passes via line 51 to a sampling point 52 at which the main flow passes via line 53 to a catalytic hydrogenation facility, hereinafter termed hydrotreater 54 for brevity. Alternatively, product leaving the hydrotreater 54 via line 59, which passes to a catalytic cracking unit (not shown) via line 60, may be sampled via line 57 and valve 56.

An automatic high performance liquid chromatographic analyzing and control unit 61, embodying equipment of the type described herein with particular reference to FIG. 3, analyzes the samples of unprocessed feed from line 55 or processed feed from line 57, and regulates the operation of the hydrotreatment unit 50 so that the feed in line 60 has an acceptable quality. Used samples are discharged via line 62.

The HPLC unit 61 (either procedure A or procedure B) has a regulatory influence on at leat the following (inter alia):
(a) the flow rate of feed through the hydrotreater and thereby the residence time or space velocity;
(b) the ratio of hydrogen to feed in the hydrotreater 54 as determined by a hydrogen control unit 63. As has already been stated herein, hydrogen is relatively expensive and an economic balance is preferably to be struck by comparing the cost of hydrogen usage with the increased value of hydrogenated feedstock. The hydrogen control unit 63 plays a part in achieving this economic balance.
(c) the operating temperatures of the hydrotreater 54 as determined by a temperature control unit 64. Higher operating temperatures increase the removal of heteroatoms (such as nitrogen) in polar molecules which tend to reduce the activity of the catalytic cracking unit while lower operating temperatures increase the saturation of aromatic rings in molecules containing them. An economic balance must be struck between the value of a processed feedstock of reduced polar molecule content and the value of the processed feedstock of lower saturated aromatic ring content. The temperature control unit 64 plays a part in achieving this overall balance.

The settings of each of the feed rate, the hydrogen control unit 63 and the temperature control unit 64 may each be adjusted by manual operation or by automatic operation or by a combination of manual and automatic operation. When automatic control of one or more settings is employed, the control may be by means of a computer (not shown) of conventional type. Suitable programs for a control computer to govern part or all of the operations of unit 50 can be devised by any competent programmer. Neither the control computer nor the software therefor will be described because both fall within the present state of the art and neither is directly germane to the present invention as defined by the appended claims.

The operation of the catalytic hydrotreatment unit 50 is now described with particular reference to preparing an upgraded catalytic cracker feedstock from a feed obtained from a vacuum distillation tower (not shown).

The raw feed in line 51 is initially passed, at least in a major proportion, via line 53 to the hydrotreater, and then via line 59 to the cat cracker feedline 60. Samples of the feed in line 55 and the product in line 57 are passed periodically (e.g., once every 60 minutes) and alternately to the HPLC unit 61 and therein analyzed for saturates, mono- and multi-aromatic ring molecules and polar molecules (which latter will contain heteroatoms such as nitrogen and oxygen). The analysis by the HPLC unit 61 is effected in the manner herein described in general, and also in particular with reference in FIGS. 3 and 4. From the analysis in the unit 61, signals are derived in signal lines 67 and 68, representative of the composition of the raw feed.

Information on the feed may be used in a "feed-forward" control sense to set the best estimated conditions of flow rate, temperature and hydrogen pressure in the hydrotreater.

If the product in line 59 has an unacceptably high content of multi-ring aromatic molecules and polar molecules, the hydrogen control unit 63 operates to increase the partial pressure of hydrogen and the ratio of hydrogen to raw feed in the hydrotreater 54 subject to programmed cost constraint signals to the unit 63 provided from the control computer via signal line 69.

The normal setting of the temperature control unit 64 is that appropriate for the saturation of aromatic nuclei, i.e., a relatively low hydrotreating temperature within the range of from about 300° C. to 510° C. The normal setting, however, is subject to modulation by signals from the control computer which reach the temperature control unit 64 via signal line 70 to increase the hydrotreating temperature in order to reduce the heteroatom content (i.e., polar molecule content) of the raw feed to an acceptable level commensurate with an acceptable level of saturation of aromatic rings in the raw feed.

The setting of the valve 56 may be varied by human intervention or by a signal from the control computer (signal line 71) to the stream and frequency at which it is analyzed.

Some additional illustrations of the method disclosed herein are now given in the following non-limitative examples.

EXAMPLE 1

Production of Lube Basestock

The objective in producing lube basestock is to separate molecules from a feedstock which has good lubricating properties, principally including a high viscosity index. Saturated hydrocarbons and aromatics not exceeding one ring are most desirable. Two of the important steps in the production of a heavy lubestock of the type known as brightstock are: deasphalting a vacuum resid with propane to produce a deasphalted oil, and extraction of the condensed ring aromatics and resins from the deasphalted oil with a polar solvent such as phenol to produce a raffinate. The asphalt produced in the first step and the aromatics-rich extract produced in the second are byproducts which have other uses. HPLC techniques as described herein are used to monitor the molecular composition of each stream and to regulate the process conditions to achieve the highest yield o raffinate within quality specifications which are based on molecular composition.

Samples of each process stream were obtained and analyzed according to the description of FIGS. 3 and 4. The evaporative light-scattering detector was employed. It was linearized according to equations (2) and (3) above by measuring its peak response to known concentrations of a vacuum gas oil. The integrated level of each component, whose retention time limits are defined by model components, is given in terms of weight percent of total sample in Table VI.

Observations of the data suggest process modifications which will be obvious to those skilled in production of lube basestock. The rejected asphalt stream from the deasphalting step contains 15.7% saturates. Some or all of these could be included in the deasphalted oil by lowering the temperature or increasing the treat ratio (i.e., the solvent to feedstock ratio) in the deasphalter. The deasphalted oil contains amounts of 3- and 4-ring aromatics which are below the detection limit but which are concentrated in the extract. The extraction step was effective at removing the 2-, 3- and 4-ring aromatics from the raffinate, but there is a trace amount of resins (polar compounds) remaining and some saturates were also removed. The selectivity of this separation could be improved by increasing the treat ratio, for example. It is assumed that process changes are made by balancing the cost of making the change versus the benefits in improved product quality or quantity.

TABLE VI

MOLECULAR COMPOSITION OF LUBE STOCKS (%)

|  | Resid | Asphalt | Deasphalted Oil | Extract | Raffinate |
|---|---|---|---|---|---|
| Saturates | 30.0 | 15.7 | 60.5 | 19.1 | 75.2 |
| Aromatics 1 | 19.4 | 14.6 | 28.8 | 34.5 | 22.6 |
| Aromatics 2 | 7.8 | 7.7 | 5.8 | 17.4 | 0.0 |
| Aromatics 3 | 2.9 | 5.7 | 0.0 | 10.1 | 0.0 |
| Aromatics 4 | 2.2 | 4.9 | 0.0 | 8.1 | 0.0 |
| Polars | 37.8 | 51.4 | 2.7 | 8.9 | 0.5 |

EXAMPLE 2

Production of Cat Cracking Feedstocks

A heavy vacuum gas oil and a heavy coker gas oil are produced by vacuum distillation and a fluid coking process, respectively. These streams are found to be too high in sulfur, nitrogen, 3+-ring aromatics, and polars for efficient cat cracking. They are, therefore, blended and subjected to a hydrotreating process wherein they are passed through two reactors in series. Both reactors are loaded with a commercial Co—Mo on alumina hydrotreating catalyst. The feed is comingled with hydrogen gas at a partial pressure of 1200 psi (8278 kPa) and the average bed temperature is 705° F. (373.9° C.). The residence time is about 22 minutes in each reactor.

The molecular composition of the feed is compared to the product of the first reactor and the second series reactor by the HPLC method of the invention. The separation is effected by the method described with reference to FIGS. 3 and 4. The detector is a UV diode array spectrophotometer. The integrated oscillator strength is calculated as in equation (1) above and converted to weight percent of aromatic carbon by the correlation of FIG. 1. The composition of each stream is given in Table 4. It is apparent that the feedstock is upgraded across each reactor. The net upgrade results in a content of 3+-ring aromatics and polars which is only about half of the starting level. Both 1- and 2-ring aromatics are produced by hydrogenation of the polynuclear aromatics.

The information available in Table VII may be used to regulate the process. If the product level of 3+-ring aromatics plus polars is below a set point determined to provide good cat cracker feedstock, the plant operator may decide either to decrease the residence time through both reactors or to bypass the second reactor altogether, for example. Other common means of control would be to vary hydrogen partial pressure or temperature or both.

TABLE VII

MOLECULAR COMPOSITIONS AS AFFECTED BY HYDROTREATING UPGRADE
(UNITS ARE WEIGHT PERCENT AROMATIC CARBON)

| Component | Feed | First Reactor Product | Second Reactor Product |
|---|---|---|---|
| 1-Ring Aromatic Core | 3.7 | 5.6 | 6.7 |
| 2-Ring Aromatic Core | 5.0 | 6.4 | 6.7 |
| 3-Ring Aromatic Core | 5.5 | 6.0 | 4.7 |
| 4-Ring Aromatic Core | 8.9 | 5.2 | 3.7 |
| Polar Core | 10.0 | 6.2 | 5.0 |

The invention defined by the appended claims is not confined to the specific embodiments herein disclosed. Moreover, any feature which is described in connection with one embodiment may be employed with any other embodiment without departing from the invention as defined by the appended claims. It is further remarked that the UV detection technique. disclosed herein, deriving the integrated oscillator strength, may be used alone, in HPLC for determining the level of aromatic carbon present, or in HPLC in combination with the mass sensitive measuring technique (using at least weak and strong eluting solvents) for measuring the level of saturates, aromatics and polars in the oil sample.

What is claimed is:

1. A method for quantifying the aromatic core content of a hydrocarbon containing solution containing more than one aromatic compound comprising the steps of:
    (a) passing a solution of hydrocarbon oil and a carrier phase in contact with a chromatographic stationary phase over a first time interval so as to retain components of siad hydrocarbon oil on said stationary phase;
    (b) passing a mobile phase in cotact with said stationary phase after step (a) over a second time interval, for eluting different retained components of said oil from said stationary phase at different time intervals, and recovering the mobile phase which has contacted the stationary phase together with the compnents eluted from the stationary phase;
    (c) irradiating recovered solution with UV light having a wavelength range of which at least a portion is within the range of about 200 nm to about 500 nm,
    (d) measuring the absorbance of the UV light by the aromatic cores in the recovered solution,
    (e) deriving the integral of absorbance as a function of photon energy across the energy corresponding to the wavelength range, and
    (f) comparing the absorbance integral to a predetermined value, thereby quantifying the aromatic core content.

2. The method of claim 1 wherein the integral of absorbance is derived as a function of photon energy across discrete portions of the energy corresponding to the wavelength range and comparing each such absorbance integral to predetermined values, thereby obtaining the ring size distribution of the aromatic cores.

3. The method of claim 1 wherein prior to step (c) the hydrocarbon solution is separated into fractions and each fraction is irradiated separately.

4. The method of claim 3 wherein separation of the hydrocarbon solution is effected by liquid chromatography.

5. The method of claim 4 wherein the separation is effected by separately eluting aromatic compounds; saturated compounds; heteroatomic, polar, and asphaltenic compounds; and polar and asphaltenic compounds, to the extent the foregoing are present in the hydrocarbon oil.

6. The method of claim 5 wherein the chromatographic separation comprises (i) a single stationary phase, (ii) a solvent of solubility parameter ranging from 7.6 to 8.8 cal$^{0.5}$/cm$^{1.5}$ for eluting aromatic compounds and saturated compounds, (iii) a strong solvent of solubility parameter ranging from 8.9 to 10.0 cal$^{0.5}$/cm$^{1.5}$ for eluting heteroatomic, polar, and asphaltenic compounds; and (iv) the strong solvent and a hydrogen bonding solvent immiscible therewith for eluting polar-, and asphaltenic compounds.

7. The method of claim 6 wherein the hydrocarbon solution is free of asphaltenes and steps (iii) and (iv) are free of asphaltenes.

8. The method of claim 6 wherein the hydrogen bonding solvent is iso-propanol.

9. The method of claim 4 wherein the separation is effected by separately eluting saturated compounds; mono-aromatic compounds; 2-ring aromatic compounds; 3-ring aromatic compounds; 4-ring aromatic compounds; and polar compounds, to the extent the foregoing are present in the hydrocarbon oil.

10. The method of claim 9 wherein the chromatographic separation comprises (i) a first and second stationary phase; (ii) a solvent of solubility parameter 7.0 to 7.8 cal$^{0.5}$/cm$^{1.5}$ is used to elute saturates and at least a portion of the mono aromatics from the first stationary phase and completing the elution of mono aromatics from the second stationary phase; (iii) eluting 2-ring aromatics from the first stationary phase; (iv) increasing solvent strength by adding a strong solvent of solubility parameter 8.9 to 10.0 cal$^{0.5}$/cm$^{1.5}$ and eluting 3-ring aromatics; (v) further increasing solvent strength by adding more of the strong solvent and eluting 4-ring aromatics; (vi) adding more strong solvent and a hydrogen bonding solvent and eluting polars; (vii) returning each stationary phase substantially to initial activity.

11. A method for the chromatographic analysis of a hydrocarbon oil comprising the steps of:
(a) passing a mixture of the hydrocarbon oil and a carrier phase in contact with a first and second stationary phase over a time interval so as to retain the components of the hydrocarbon oil on the stationary phases wherein the first stationary phase comprises surface hydroxyl groups substantially all of which have been substantially fully functionalized with a charge transfer functionality selected from the group consisting of trinitroanilino propane, tetrachlorophthalimido propane, dinitrobenzoyl glycidyl propane and tetranitrofluorenone and the second stationary phase comprises surface hydroxyl groups at least a portion of which have been substantially fully functionalized by a functionality selected from the group consisting of aminopropyl, cyanopropyl, nitropropyl and a combination thereof;
(b) passing in contact with the first and second stationary phases a mobile phase of a weak solvent having a solubility parameter of 7.0 to 7.8 cal$^{0.5}$/cm$^{1.5}$ for a second time interval sufficient to elute saturates and mono aromatics from the first stationary phase;
(c) continuing passing the weak solvent to the second stationary phase for a third time interval sufficient to complete substantially the elution of mono aromatics;
(d) recovering solvent passed to the first and second stationary phases;
(e) monitoring solvents recovered in step (d) and detecting at least saturates, mono aromatics, and aromatics of 2 or more rings.

12. The method of claim 11 wherein the hydrocarbon oil contains n+2 ring aromatics and solvent strength is increased n+2 times, passed to the first stationary phase in n+2 intervals, and aromatics having n+2 rings are eluted, wherein n equals 0 to 2.

13. The method of claim 12 wherein solvent strength is increased by replacing at least a portion of the weak solvent with a strong solvent having a solubility parameter of 8.9 to 10.0 ca$^{0.5}$/cm$^{1.5}$.

14. The method of claim 12 wherein the hydrocarbon oil contains polar compounds and solvent strength is further increased, passed to the first stationary phase in an additional time interval to elute polar compounds.

15. The method of claim 14 wherein a hydrogen bonding solvent is added for the elution of polar compounds.

16. The method of claim 14 wherein solvent strength is increased in steps (e), (f), and (g) by replacing at least a portion of the weak solvent with a strong solvent having a solubility parameter of 8.9 to 10.0 cal$^{0.5}$/cm$^{1.5}$.

17. A method for the chromatographic analysis of a hydrocarbon oil comprising the steps of:
(a) passing a mixture of the hydrocarbon oil and a carrier phase in contact with a first and second chromatographic stationary phase over a time interval so as to retain the components of the hydrocarbon oil on the stationary phases;
(b) passing in contact with the first and second stationary phases a first mobile phase of a weak solvent having a solubility parameter from 7.0 to 7.8 cal$^{0.5}$/cm$^{1.5}$ for a second time interval sufficient to elute saturates and mono aromatics from the first stationary phase;
(c) bypassing the first stationary phase and continuing passing the weak solvent to the second stationary phase for a third time interval sufficient to complete substantially the elution of mono aromatics;
(d) bypassing the second stationary phase and passing the weak solvent to the first stationary phase for a fourth time interval sufficient to elute 2-ring aromatics;
(e) passing solvent of increased strength to the first stationary phase for a fifth time interval sufficient to elute 3-ring aromatics;
(f) passing solvent of a strength greater than in step (e) to the first stationary phase for a sixth time interval sufficient to elute 4-ring aromatics;
(g) passing solvent of a strength greater than in step (f) to the first stationary phase for a seventh time interval sufficient to elute polar compounds;
(h) recovering the solvent from each of steps (b)-(g);
(i) monitoring the solvents recovered in step (h) and detecting saturates, mono aromatics, 2-ring aromatics, 3-ring aromatics, 4-ring aromatics, and polars.

18. The method of claim 17 wherein the hydrogen bonding solvent is isopropanol.

19. The method of claim 16 wherein the first stationary phase comprises surface hydroxyl groups substantially all of which have been substantially fully functionalized with a charge transfer functionality selected from the group consisting of trinitroanilino propane, tetrachlorophthalimido propane, dinitrobenzoyl glycidyl propane and tetranitrofluorenone and the second stationary phase comprises surface hydroxyl groups at least a portion of which have been substantially fully functionalized by a functionality selected from the group consisting of aminopropyl, cyanopropyl, nitropropyl and a combination thereof.

20. The method of claim 17 wherein subsequent to step (g) the strong solvent is passed to the first stationary phase for a period sufficient to remove substantially all of the hydrogen bonding solvent.

21. The method of claim 20 wherein the weak solvent is passed to the first and second stationary phases for a period sufficient to restore substantially initial activity.

22. The method of claim 21 wherein the weak solvent is passed independently to each of the first and second stationary phases.

23. The method of claim 17 wherein the weak and strong solvents have less than 1 ppm water.

* * * * *